United States Patent
Fischer et al.

(10) Patent No.: US 6,774,133 B2
(45) Date of Patent: Aug. 10, 2004

(54) SUBSTITUTED SPIROHETEROCYCLIC 1H-3-ARYL-PYRROLIDINE-2,4-DIONE DERIVATIVES, PROCESSES FOR THEIR PREPARATION, AND THEIR USE AS PESTICIDES

(75) Inventors: Reiner Fischer, Monheim (DE); Thomas Bretschneider, Lohmar (DE); Bernd-Wieland Krüger, Bergisch Gladbach (DE); Hans-Joachim Santel, Leverkusen (DE); Markus Dollinger, Leverkusen (DE); Christoph Erdelen, Leichlingen (DE); Ulrike Wachendorff-Neumann, Neuwied (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/372,417

(22) Filed: Feb. 24, 2003

(65) Prior Publication Data

US 2004/0009999 A1 Jan. 15, 2004

Related U.S. Application Data

(62) Division of application No. 10/175,125, filed on Jun. 19, 2002, now Pat. No. 6,555,567, which is a division of application No. 09/325,063, filed on Jun. 3, 1999, now Pat. No. 6,479,489, which is a division of application No. 08/578,519, filed as application No. PCT/EP94/01997 on Jun. 20, 1994, now Pat. No. 5,981,567.

(30) Foreign Application Priority Data

| Jul. 2, 1993 | (DE) | ...................................... | P 43 22 052 |
| Jan. 7, 1994 | (DE) | ...................................... | P 44 00 223 |
| May 2, 1994 | (DE) | ...................................... | P 44 15 334 |

(51) Int. Cl.$^7$ ........................ A01N 43/42; C07D 221/20
(52) U.S. Cl. ......................................... 514/278; 546/16
(58) Field of Search ............................. 514/278; 546/16

(56) References Cited

U.S. PATENT DOCUMENTS 4,585,881 A 4/1986 Becker et al.

| 5,045,560 A | 9/1991 | Fischer et al. |
| 5,186,737 A | 2/1993 | Fischer et al. |
| 5,191,089 A | 3/1993 | Fisher et al. |
| 5,258,527 A | 11/1993 | Krauskopt et al. |
| 5,350,861 A | 9/1994 | Fischer et al. |
| 5,462,913 A | 10/1995 | Fischer et al. |
| 5,616,536 A | 4/1997 | Fischer et al. |

FOREIGN PATENT DOCUMENTS

| EP | 0 121 129 | 10/1984 |
| EP | 0 456 063 | 11/1991 |
| EP | 0 497 127 | 8/1992 |
| EP | 0 521 334 | 1/1993 |
| EP | 0 595 130 | 5/1994 |
| EP | 0 596 298 | 5/1994 |
| EP | 0 613 884 | 9/1994 |

OTHER PUBLICATIONS

Cram and Hammond, "Organic Chemistry", $2^{nd}$ Ed. (1994) NTY; McGraw–Hill Book Co.

*Primary Examiner*—Patricia L. Morris
(74) *Attorney, Agent, or Firm*—Norris McLaughlin & Marcus PA

(57) ABSTRACT

The invention concerns substituted spiro heterocyclic 1H-3-arylpyrrolidine-2,4-dione derivatives depicted by the formula:

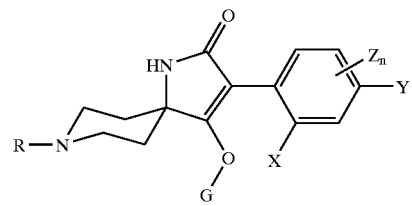

X is alkyl, halogen or alkoxy; Y is hydrogen, alkyl, halogen, alkoxy or alkyl halide; Z is alkyl, halogen or alkoxy; n is 0, 1, 2 or 3; G is hydrogen (a) or one of the groups (b), (c), (d), (e), (f) or (g) as defined in the specification. The invention also concerns methods of preparing the substituted spiro heterocyclic 1H-3-arylpyrrolidine-2,4-dione derivative compounds, intermediate compounds thereof and use of substituted spiro heterocyclic 1H-3-arylpyrrolidine-2,4-dione derivative compounds as pest-control agents.

11 Claims, No Drawings

SUBSTITUTED SPIROHETEROCYCLIC 1H-3-ARYL-PYRROLIDINE-2,4-DIONE DERIVATIVES, PROCESSES FOR THEIR PREPARATION, AND THEIR USE AS PESTICIDES

This application is a divisional application of U.S. Ser. No. 10/175,125, filed on Jun. 19, 2002, now U.S. Pat. No. 6,555,567, which in turn is a divisional of U.S. Ser. No. 09/325,063, filed on Jun. 3, 1999, now U.S. Pat. No. 6,479,489, which in turn is a divisional application of U.S. Ser. No. 08/578,519, filed on Dec. 28, 1995, now U.S. Pat. No. 5,981,567, which in turn was a national phase application of PCT/EP94/01997, filed on Jun. 20, 1994.

The invention relates to new substituted spirocyclic 1H-3-aryl-pyrrolidine-2,4-dione derivatives, to a plurality of processes for their preparation, and to their use as pesticides and as herbicides.

3-Acyl-pyrrolidine-2,4-diones have already been described as having pharmaceutical properties (S. Suzuki et al. Chem. Pharm. Bull. 15 1120 (1967)). Furthermore, N-phenyl-pyrrolidine-2,4-diones were synthesized by R. Schmierer and H. Mildenberger (Liebigs Ann. Chem. 1985 1095). These compounds were not described as having a biological activity. There have also been described 5-vinyl-tetramic acids which have pharmaceutical properties (GB-A 22 66 888).

EP-A 0 262 399 discloses 3-aryl-pyrrolidine-2,4-diones, but nothing has been disclosed about them having a herbicidal, insecticidal or acaricidal action. A herbicidal, insecticidal or acaricidal action has been disclosed in the case of unsubstituted bicyclic 3-aryl-pyrrolidine-2,4-dione derivatives (EP-A 355 599) and (EP 415 211) and of substituted monocyclic 3-aryl-pyrrolidine-2,4-dione derivatives (EP-A 377 893), (EP 442 077), (EP 497 127) and substituted bicyclic 3-aryl-pyrrolidone derivatives (EP 501 129).

Other compounds which have been disclosed are polycyclic 3-arylpyrrolidine-2,4-dione derivatives (EP 442 073) and 1H-3-arylpyrrolidine-dione derivatives (EP 456 063) and (EP 521 334).

There have now been found new substituted spirocyclic 1H-3-aryl-pyrrolidine-2,4-dione derivatives of the formula (I)

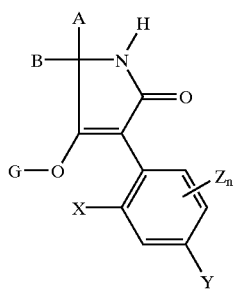

(I)

in which

A and B together with the carbon atom to which they are bonded represent an unsubstituted or substituted 5–6-membered cycle which is interrupted by at least one hetero atom, X represents alkyl, halogen or alkoxy, Y represents hydrogen, alkyl, halogen, alkoxy or halogenoalkyl, Z represents alkyl, halogen or alkoxy, n represents a number 0, 1, 2 or 3, G represents hydrogen (a) or the groups

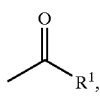 (b)

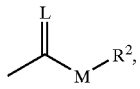 (c)

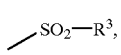 (d)

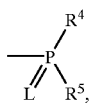 (e)

E or (f)

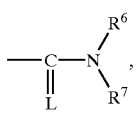 (g)

E represents a metal ion equivalent or an ammonium ion,

L and M in each case represent oxygen or sulphur, $R^1$ represents alkyl, alkenyl, alkoxyalkyl, alkylthioalkyl, polyalkoxyalkyl or cycloalkyl which can be interrupted by hetero atoms, each of these radicals optionally being substituted by halogen, or represents in each case optionally substituted phenyl, phenylalkyl, hetaryl, phenoxyalkyl or hetaryloxyalkyl, $R^2$ represents in each case optionally substituted alkyl, cycloalkyl, alkenyl, alkoxyalkyl, polyalkoxyalkyl or in each case optionally substituted phenyl or benzyl, $R^3$, $R^4$ and $R^5$ independently of one another represent alkyl, alkoxy, alkylamino, dialkylamino, alkylthio, alkenylthio, cycloalkylthio, each of which is optionally substituted by halogen, or represent in each case optionally substituted phenyl, phenoxy or phenylthio, $R^6$ and $R^7$ independently of one another represent hydrogen, or alkyl, cycloalkyl, alkenyl, alkoxy, alkoxyalkyl, each of which is optionally substituted by halogen, or represent optionally substituted phenyl or optionally substituted benzyl, or together with the N atom to which they are bonded represent a cycle which is optionally interrupted by oxygen or sulphur.

Taking into consideration the various meanings (a), (b), (c), (d), (e) and (f) of group G in the general formula (I), the following main structures (Ia) to (Ig) result:

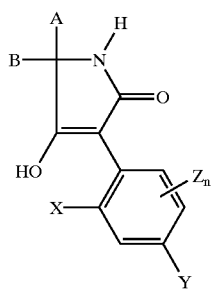
(Ia)

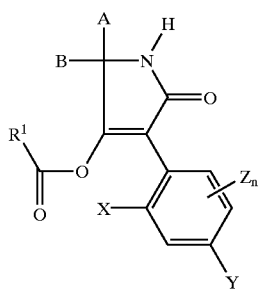
(Ib)

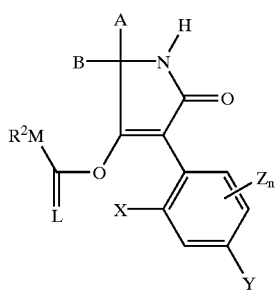
(Ic)

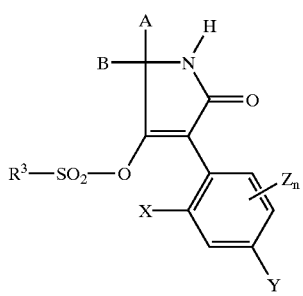
(Id)

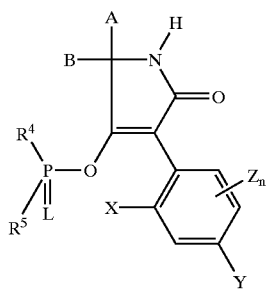
(Ie)

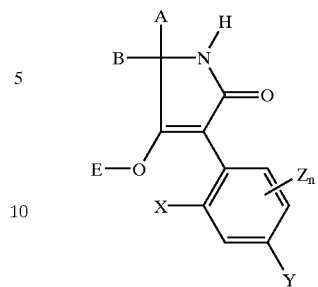
(If)

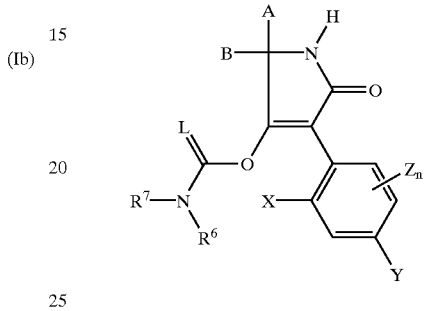
(Ig)

in which

A, B, E, L, M, Y, Z, $R^1$, $R^2$, $R^3$, $R^4$, $R^5$, $R^6$, $R^7$ and n have the abovementioned meanings.

Due to one or more chiral centres, the compounds of the formula (Ia)–(Ig) are generally obtained in the form of a stereoisomer mixture. They can be used in the form of their diastereomer mixtures or as the pure diastereomers or enantiomers.

Furthermore, it has been found that the new substituted 1H-3-aryl-pyrrolidine-2,4-dione derivatives of the formula (I) are obtained by one of the processes described hereinbelow.

(A) 1H-3-Aryl-pyrrolidine-2,4-diones or their enols of the formula (Ia)

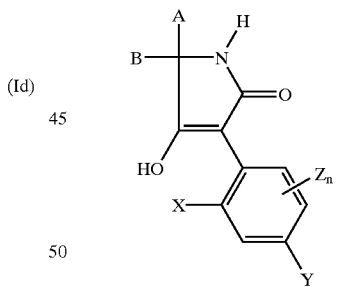
(Ia)

in which

A, B, X, Y, Z and n have the abovementioned meaning, are obtained when N-acylamino acid esters of the formula (II)

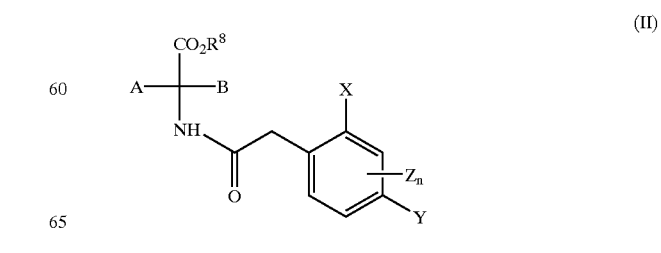
(II)

in which
A, B, X, Y, Z and n have the abovementioned meaning
and
$R^8$ represents alkyl, are subjected to an intramolecular condensation reaction in the presence of a diluent and in the presence of a base; or (B) compounds of the formula (Ib)

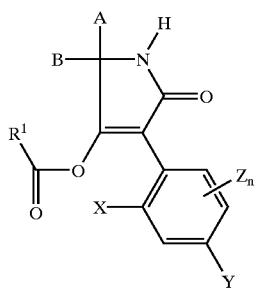

(Ib)

in which
A, B, X, Y, Z, $R^1$ and n have the abovementioned meaning, are obtained when compounds of the formula (Ia)

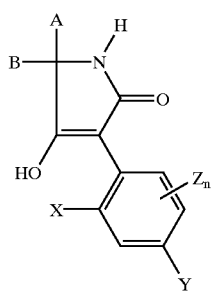

(Ia)

in which
A, B, X, Y, Z and n have the abovementioned meaning,

α) are reacted with acid halides of the formula (III)

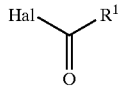

(III)

in which
$R^1$ has the abovementioned meaning and
Hal represents halogen, in particular chlorine and bromine, if appropriate in the presence of a diluent and if appropriate in the presence of an acid-binding agent or β) are reacted with carboxylic anhydrides of the formula (IV)

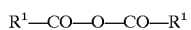

$R^1$—CO—O—CO—$R^1$ (IV)

in which
$R^1$ has the abovementioned meaning, if appropriate in the presence of a diluent and if appropriate in the presence of an acid-binding agent; or (C) compounds of the formula (Ic-1)

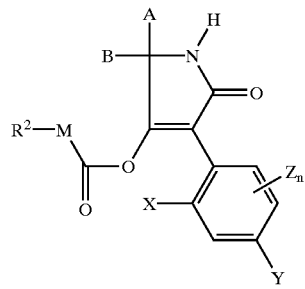

(Ic-1)

in which
A, B, X, Y, Z, $R^2$ and n have the abovementioned meaning, and
M represents oxygen or sulphur are obtained when compounds of the formula (Ia)

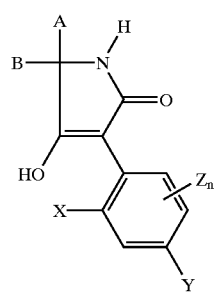

(Ia)

in which
A, B, Y, Z and n have the abovementioned meaning, are reacted with chloroformic ester or chloroformic thiol ester of the formula (V)

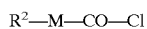

$R^2$—M—CO—Cl (V)

in which
$R^2$ and M have the abovementioned meaning, if appropriate in the presence of a diluent and if appropriate in the presence of an acid-binding agent; or (D) compounds of the formula (Ic-2)

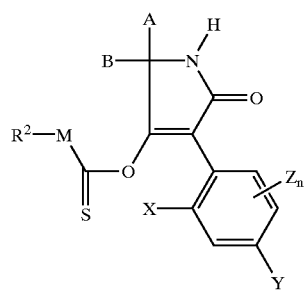

(Ic-2)

in which
A, B, $R^2$, X, Y, Z and n have the abovementioned meaning and
M represents oxygen or sulphur, are obtained ashen compounds of the formula (Ia)

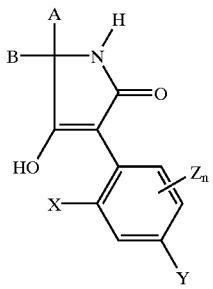
(Ia)

in which
A, B, X, Y, Z and n have the abovementioned meaning,

α) are reacted with chloromonothioformic esters or chlorodiothioformic esters of the formula (VI)

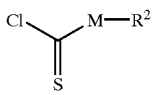
(VI)

in which
M and R² have the abovementioned meaning, if appropriate in the presence of a diluent and if appropriate in the presence of an acid-binding agent, or β) are reacted with carbon disulphide and subsequently with alkyl halides of the general formula (VI)

R²—Hal (VII)

in which
R² has the abovementioned meaning and
Hal represents chlorine, bromine or iodine, if appropriate in the presence of a diluent and if appropriate in the presence of an auxiliary base; or (E) compounds of the formula (Id)

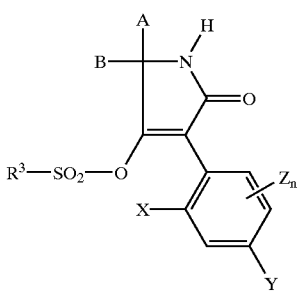
(Id)

in which
A, B, X, Y, Z, R³ and n have the abovementioned meaning, are obtained when compounds of the formula (Ia)

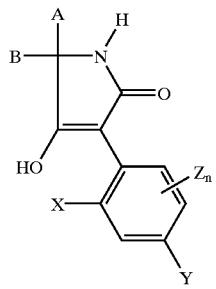
(Ia)

in which
A, B, X, Y, Z and n have the abovementioned meaning,
are reacted with sulphonyl chlorides of the formula (VI)

R³—SO₂—Cl (VIII)

in which
R³ has the abovementioned meaning,
if appropriate in the presence of a diluent and if appropriate in the presence of an acid-binding agent; or (F) 3-aryl-pyrrolidine-2,4-diones of the formula (Ie)

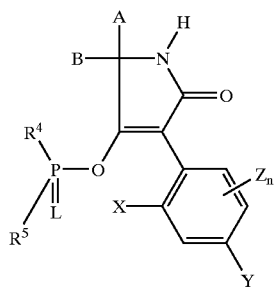
(Ie)

in which
A, B, L, X, Y, Z, R⁴, R⁵ and n have the abovementioned meaning,
are obtained when 1-H-3-aryl-pyrrolidine-2,4-diones of the formula (Ia) or their enols

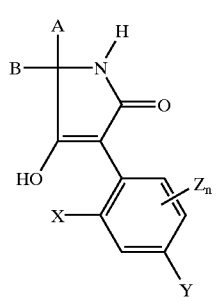
(Ia)

in which
A, B, X, Y, Z and n have the abovementioned meaning,
are reacted with phosphorus compounds of the formula (IX)

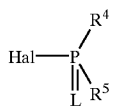

in which
L, $R^4$ and $R^5$ have the abovementioned meaning and
Hal represents halogen, in particular chlorine and bromine, if appropriate in the presence of a diluent and if appropriate in the presence of an acid-binding agent; or (G) compounds of the formula (If)

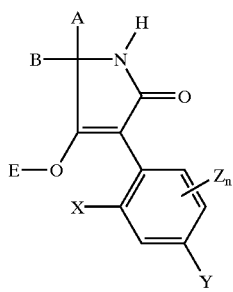

(I-f)

in which
A, B, X, Y, Z and n have the abovementioned meaning, and
E represents a metal ion equivalent or an ammonium ion, are obtained when compounds of the formula (Ia)

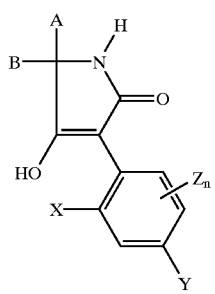

(Ia)

in which
A, B, X, Y, Z and n have the abovementioned meaning,
are reacted with metal compounds or amines of the formulae (X) and (XI)

(X)

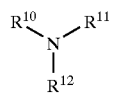

(XI)

in which
Me represents mono- or divalent metal ions,
t represents the number 1 or 2,
$R^{10}$, $R^{11}$ and $R^{12}$ independently of one another represent hydrogen or alkyl and
$R^{13}$ represents hydrogen, hydroxyl or $C_1$–$C_4$-alkoxy, if appropriate in the presence of a diluent.

(H) Furthermore, it has been found that compounds of the formula (I-g)

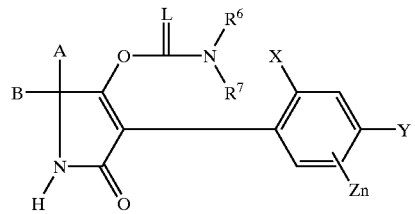

(I-g)

in which
A, B, L, X, Y, Z, $R^6$, $R^7$ and n have the abovementioned meaning, are obtained, when compounds of the formula (Ia)

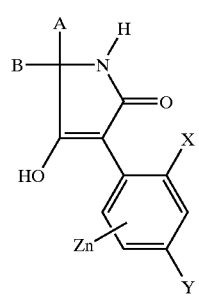

(Ia)

in which
A, B, X, Y, Z and n have the abovementioned meaning,
are reacted

α) with compounds of the formula (XII)

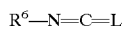

$R^6$—N=C=L (XII)

in which
L and $R^6$ have the abovementioned meaning
if appropriate in the presence of a diluent and if appropriate in the presence of a catalyst or β) with carbamoyl chlorides or thiocarbamoyl chlorides of the formula (XIII)

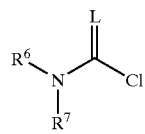

(XIII)

in which
L, $R^6$ and $R^7$ have the abovementioned meaning
if appropriate in the presence of a diluent and if appropriate in the presence of an acid-binding agent.

Furthermore, it has been found that the new 1H-3-arylpyrrolidine-2,4-dione derivatives of the formula (I) are distinguished by outstanding insecticidal, acaricidal and herbicidal actions.

In the general formulae of the present application,
A, B and the carbon atom to which they are bonded preferably represent a 5–6-membered spirocycle which contains the group

and/or oxygen and/or sulphur and which can be unsubstituted or monosubstituted or polysubstituted by alkyl, cycloalkyl, haloalkyl, alkoxy, thioalkyl, halogen or phenyl.

A, B and the carbon to which they are bonded particularly preferably represent a 5–6-membered spirocycle which contains the group

and/or oxygen and/or sulphur and which can be unsubstituted or monosubstituted or polysubstituted by $C_1$–$C_6$alkyl, $C_1$–$C_8$-cycloalkyl, $C_1$–$C_3$-haloalkyl, $C_1$–$C_4$-alkoxy, $C_1$–$C_4$-thioalkyl, fluorine, chlorine or phenyl.

A, B and the carbon atom to which they are bonded very particularly preferably represent a 5–6-spirocycle which contains the group

and/or oxygen and/or sulphur and which can be unsubstituted or monosubstituted or polysubstituted by methyl, ethyl, propyl, isopropyl, butyl, iso-butyl, sec-butyl, tert-butyl, cyclohexyl, trifluoromethyl, methoxy, methylthio, fluorine, chlorine or phenyl.

X preferably represents $C_1$–$C_6$-alkyl, halogen or $C_1$–$C_6$-alkoxy.

X very particularly represents $C_1$–$C_4$-alkyl, halogen or $C_1$–$C_4$-alkoxy.

X very particularly preferably represents methyl, ethyl, propyl, 2-propyl, fluorine, chlorine, bromine, methoxy or ethoxy.

Y preferably represents hydrogen, $C_1$–$C_6$-alkyl, halogen, $C_1$–$C_6$-alkoxy or $C_1$–$C_3$-halogenoalkyl.

Y particularly preferably represents hydrogen, $C_1$–$C_4$-alkyl, halogen, $C_1$–$C_4$-alkoxy or $C_1$–$C_2$-halogenoalkyl.

Y very particularly preferably represents hydrogen, methyl, ethyl, propyl, i-propyl, butyl, i-butyl, tert-butyl, fluorine, chlorine, bromine, methoxy, ethoxy or trifluoromethyl.

Z preferably represents $C_1$–$C_6$alkyl, halogen or $C_1$–$C_6$alkoxy.

Z particularly preferably represents $C_1$–$C_4$-alkyl, halogen or $C_1$–$C_4$-alkoxy.

Z very particularly preferably represents methyl, ethyl, propyl, i-propyl, butyl, i-butyl, tert-butyl, fluorine, chlorine, bromine, methoxy or ethoxy.

G preferably represents hydrogen (a) or the groups

(b)

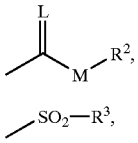

(c)

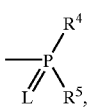

(d)

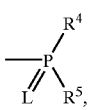

(e)

E or (f)

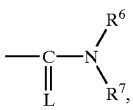

(g)

in which

E represents a metal ion equivalent or an ammonium ion and

L and M in each case represent oxygen or sulphur.

$R^1$ preferably represents $C_1$–$C_{20}$-alkyl, $C_2$–$C_{10}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_1$–$C_8$-alkyl or cycloalkyl which has 3 to 8 ring atoms and which can be substituted by $C_1$–$C_6$-alkyl and interrupted by oxygen and/or sulphur atoms, each of these radicals optionally being substituted by halogen, or represents phenyl which is optionally substituted by halogen, nitro, $C_1$–$C_6$-alkyl, $C_1$–$C_6$-alkoxy, $C_1$–$C_6$-halogenoalkyl or $C_1$–$C_6$-halogenoalkoxy, or represents phenyl-$C_1$–$C_6$alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which is optionally substituted by halogen and/or $C_1$–$C_6$-alkyl, or represents phenoxy-$C_1$–$C_6$-alkyl which is optionally substituted by halogen and/or $C_1$–$C_6$-alkyl or represents hetaryloxy-$C_1$–$C_6$-alkyl which is optionally substituted by halogen, amino and/or $C_1$–$C_6$-alkyl.

$R^2$ preferably represents $C_1$–$C_{20}$-alkyl, $C_3$–$C_{10}$-alkenyl, $C_1$–$C_8$-alkoxy-$C_2$–$C_8$-alkyl, $C_1$–$C_8$-polyalkoxy-$C_2$–$C_8$-alkyl, each of which is optionally substituted by halogen, or represents $C_3$–$C_6$-cycloalkyl which is optionally substituted by halogen or $C_1$–$C_6$-alkyl or represents phenyl or benzyl, each of which is optionally substituted by halogen, nitro, $C_1$–$C_6$-alkyl, $C_1$–$C_6$-alkoxy or $C_1$–$C_6$-halogenoalkyl.

$R^3$, $R^4$ and $R^5$ independently of one another preferably represent $C_1$–$C_8$-alkyl, $C_1$–$C_8$-alkoxy, $C_1$–$C_8$-alkylamino, di($C_1$–$C_8$)alkylamino, $C_1$–$C_8$-alkylthio, $C_3$–$C_5$-alkenylthio, $C_3$–$C_7$-cycloalkylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$- alkylthio, $C_1$–$C_4$-halogenoalkylthio, $C_1$–$C_8$-alkyl or $C_1$–$C_4$-halogenoalkyl.

$R^6$ and $R^7$ independently of one another preferably represent hydrogen, $C_1$–$C_{10}$-alkyl, $C_3$–$C_{10}$-cycloalkyl, $C_1$–$C_{10}$-alkoxy, $C_3$–$C_8$-alkenyl or $C_1$–$C_8$-alkoxy-$C_1$–$C_8$-alkyl, each of which is optionally substituted by halogen, or represent phenyl which is optionally substituted by halogen, $C_1$–$C_8$-halogenoalkyl, $C_1$–$C_8$-alkyl or $C_1$–$C_8$-alkoxy, or represent benzyl which is optionally substituted by halogen, $C_1$–$C_8$-alkyl, $C_1$–$C_8$-halogenoalkyl or $C_1$–$C_8$-alkoxy, or together with the N atom to which they are bonded represent a 3- to 7-membered ring which is optionally interrupted by oxygen or sulphur.

$R^9$ preferably represents hydrogen, $R^1$, $COR^1$ or $CO_2R^2$ where $R^1$ and $R^2$ can assume the meanings mentioned above as being preferred for $R^1$ and $R^2$, respectively.

n preferably represents a number from 0 to 3.

G particularly preferably represents hydrogen (a) or the groups

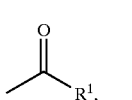
(b)

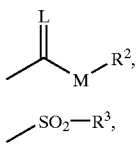
(c)

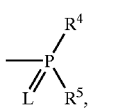
(d)

(e)

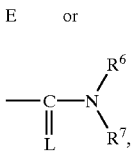

E or
(f)

(g)

in which

E represents a metal ion equivalent or an ammonium ion and

L and M in each case represent oxygen or sulphur, $R^1$ particularly preferably represents $C_1$–$C_{16}$-alkyl, $C_2$–$C_8$-alkenyl, $C_1$–$C_6$-alkoxy-$C_1$–$C_6$-alkyl, $C_1$–$C_6$-alkylthio-$C_1$–$C_6$-alkyl, $C_1$–$C_6$-polyalkoxy-$C_1$–$C_6$-alkyl or cycloalkyl which has 3 to 7 ring atoms and which can be substituted by $C_1$–$C_4$-alkyl and interupted by 1–2 oxygen and/or sulphur atoms, each of these radicals optionally being substituted by halogen, or represents phenyl which is optionally substituted by halogen, nitro, $C_1$–$C_4$-alkyl, $C_1$–$C_4$-alkoxy, $C_1$–$C_3$-halogenoalkyl or $C_1$–$C_3$-halogenoalkoxy, or represents phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy, or represents furanyl, thienyl, pyridyl, pyrimidyl, thiazolyl or pyrazolyl, each of which is optionally substituted by fluorine, chlorine, bromine and/or $C_1$–$C_4$-alkyl, or represents phenoxy-$C_1$–$C_5$-alkyl which is optionally substituted by fluorine, chlorine, bromine and/or $C_1$–$C_4$-alkyl or represents pyridyloxy-$C_1$–$C_6$-alkyl, pyrimidinyloxy-$C_1$–$C_6$-alkyl or thiazolyloxy-$C_1$–$C_6$-alkyl, each of which is optionally substituted by fluorine, chlorine, bromine, amino and/or $C_1$–$C_4$-alkyl.

$R^2$ particularly preferably represents $C_1$–$C_{16}$-alkyl, $C_3$–$C_8$-alkenyl, $C_1$–$C_6$-alkoxyl-$C_2$–$C_6$-alkyl or $C_1$–$C_6$-polyalkoxy-$C_2$–$C_6$-alkyl, each of which is optionally substituted by halogen, or represents $C_3$–$C_6$-cycloalkyl which is optionally substituted by fluorine, chlorine or $C_1$–$C_4$-alkyl or represents phenyl or benzyl, each of which is optionally substituted by halogen, nitro, $C_1$–$C_4$-alkyl, $C_1$–$C_3$-alkoxy or $C_1$–$C_3$-halogenoalkyl.

$R^3$, $R^4$ and $R^5$ independently of one another particularly preferably represent $C_1$–$C_6$-alkyl, $C_1$–$C_6$-alkoxy, $C_1$–$C_6$-alkylamino, di($C_1$–$C_6$)alkylamino, $C_1$–$C_6$-alkylthio, $C_3$–$C_4$-alkenylthio, $C_3$–$C_6$-cycloalkylthio, each of which is optionally substituted by halogen, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or represent $C_1$–$C_8$-alkyl, $C_3$–$C_8$-cycloalkyl, $C_1$–$C_8$-alkoxy, $C_3$–$C_6$-alkenyl or $C_1$–$C_6$-alkoxy-$C_1$–$C_6$-alkyl, each of which is optionally substituted by halogen, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoaklyl or $C_1$–$C_5$-alkoxy, or together with the N atom to which they are bonded represent a 4- to 7-membered ring which is optionally interrupted by oxygen or sulphur.

$R^9$ particularly preferably represents hydrogen, $COR^{1'}$ or $CO_2R^{1'}$ where $R^{1'}$ represents $C_1$–$C_6$-alkyl, phenyl or benzyl.

n particularly preferably represents a number from 0 to 2.

G very particularly preferably represents hydrogen (a) or the groups (b)

(c)

(d)

(e)

(f)

E or

-continued

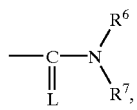
(g)

in which
E represents a metal ion equivalent or an ammonium ion and
L and M in each case represent oxygen or sulphur.
$R^1$ very particularly preferably represents $C_1$–$C_{14}$-alkyl, $C_2$–$C_6$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_1$–$C_4$-alkyl or cycloalkyl which has 3 to 6 ring atoms and which can be substituted by methyl or ethyl and interrupted by 1 to 2 oxygen and/or sulphur atoms, each of these radicals optionally being substituted by fluorine or chlorine,
or represents phenyl which is optionally substituted by fluorine, chlorine, bromine, methyl, ethyl, propyl, i-propyl, methoxy, ethoxy, trifluoromethyl, trifluoromethoxy or nitro,
or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy,
or represents thienyl, firanyl, pyridyl, pyrimidyl, thiazolyl or pyrazolyl, each of which is optionally substituted by fluorine, chlorine, bromine, methyl or ethyl,
or represents phenoxy-$C_1$–$C_4$-alkyl which is optionally substituted by fluorine, chlorine, methyl or ethyl,
or represents pyridyloxy-$C_1$–$C_4$-alkyl, pyrimidinyloxy-$C_1$–$C_4$-alkyl or thiazolyloxy-$C_1$–$C_4$-alkyl, each of which is optionally substituted by fluorine, chlorine, amino, methyl or ethyl.
$R^2$ very particularly preferably represents $C_1$–$C_{14}$-alkyl, $C_3$–$C_6$-alkenyl, $C_1$–$C_4$-alkoxy-$C_2$–$C_6$-alkyl or $C_1$–$C_4$-polyalkoxy-$C_2$–$C_6$-alkyl, each of which is optionally substituted by fluorine or chlorine, or represents $C_3$–$C_6$-cycloalkyl which is optionally substituted by fluorine, chlorine, methyl or ethyl,
or represents phenyl or benzyl, each of which is optionally substituted by fluorine, chlorine, nitro, methyl, ethyl, propyl, i-propyl, methoxy, ethoxy or trifluoromethyl.
$R^3$, $R^4$ and $R^5$ independently of one another very particularly preferably represent $C_1$–$C_4$-alkyl, $C_1$–$C_4$-alkoxy, $C_1$–$C_4$-alkylamino, di($C_1$–$C_4$)alkylamino or $C_1$–$C_4$-alkylthio, each of which is optionally substituted by fluorine or chlorine, or represent phenyl, phenoxy or phenylthio, each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl.
$R^6$ and $R^7$ independently of one another very particularly preferably represent hydrogen, or represent $C_1$–$C_6$-alkyl, $C_3$–$C_6$-cycloalkyl, $C_1$–$C_6$-alkoxy or $C_1$–$C_6$-alkoxy-$C_1$–$C_4$-alkyl, each of which is optionally substituted by fluorine, chlorine or bromine, or represent phenyl which is optionally substituted by fluorine, chlorine, bromine, $C_1$–$C_4$-halogenoalkyl, $C_1$–$C_4$-alkyl or $C_1$–$C_4$-alkoxy, or represent benzyl which is optionally substituted by fluorine, chlorine, bromine, $C_1$–$C_4$-alkyl, $C_1$–$C_4$-halogenoalkyl or $C_1$–$C_4$-alkoxy, or together with the N atom to which they are bonded represent a 5- to 7-membered ring which is optionally interrupted by oxygen or sulphur.
$R^9$ very particularly preferably represents hydrogen, $COR^{1'}$ or $COR^{1'}$ where $R^{1'}$ represents $C_1$–$C_4$-alkyl, phenyl or benzyl.

n very particularly preferably represents 0 or 1.

Due to one or more chiral centres, the compounds of the formula (Ia)–(Ig) are generally obtained in the form of stereoisomer. They can be used in the form of their diastereomer mixtures, but also as the pure diastereomers or enantiomers.

If, in accordance with process (A), ethyl 4-(2,4-dichlorophenylacetyl-amino-1-acetylpiperidine-4-carboxylate is used, the course of the process according to the invention can be represented by the following equation:

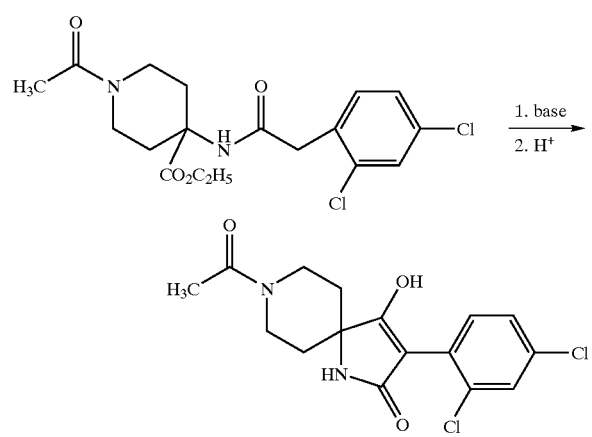

If, in accordance with process B (variant a), 3-(2,4,6-trimethylphenyl)-5,5-(ethylenethioethylene)-pyrrolidine-2,4-dione and pivaloyl chloride are used as starting materials, the course of the process according to the invention can be represented by the following equation:

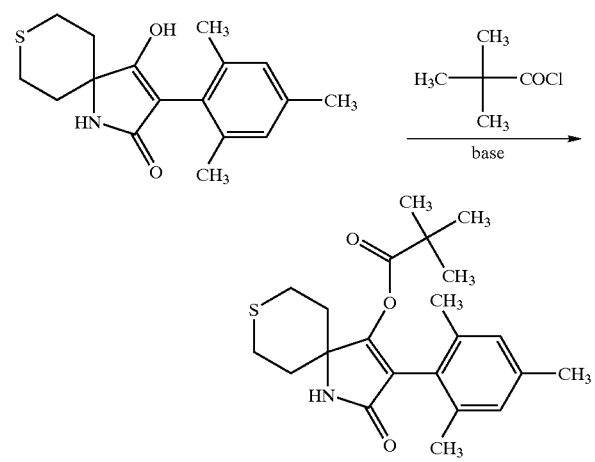

If, in accordance with process B (variant β), 3-(2,4,6-trimethylphenyl)-5,5-ethylenethiomethylene-pyrrolidine-2,4-dione and acetic anhydride are used as starting compounds, the course of the process according to the invention can be represented by the following equation:

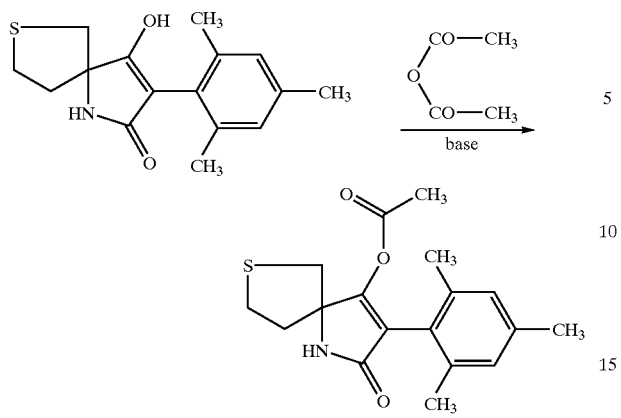

If, in accordance with process (C), 3-(2,4,6-trimethylphenyl)-5,5-ethylenethiomethylene-pyrrolidine-2,4-dione and ethoxyethyl chloroformate are used as starting compounds, the course of the process according to the invention can be represented by the following equation.

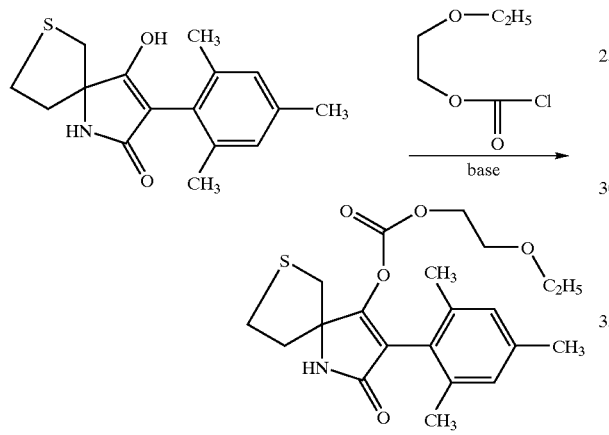

If, in accordance with process ($D_\alpha$), 3-(2,4,6-trimethylphenyl)-5,5-ethyleneoxaethylene-pyrrolidine-2,4-dione and methyl chloromonothioformate are used as starting materials, the course of the reaction can be represented as follows:

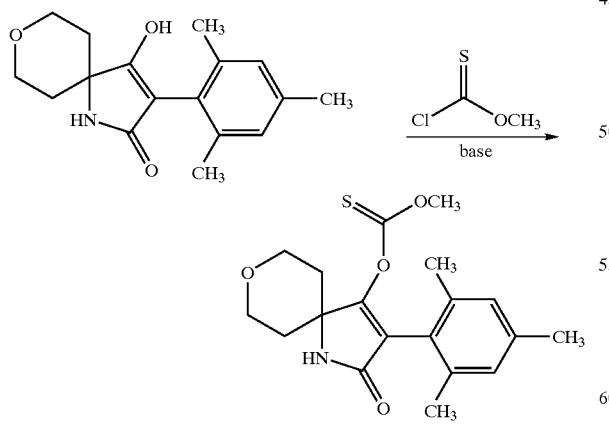

If, in accordance with process ($D_\beta$), 3-(2,4,6-trimethylphenyl)-5,5-ethylenethioethylene-pyrrolidine-2,4-dione, carbon disulphide and methyl iodide are used as starting components, the course of the reaction can be represented as follows:

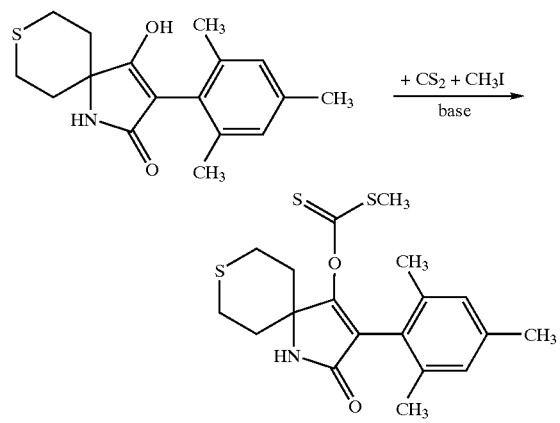

If, in accordance with process (E), 3-(2,4,6-trimethylphenyl)-5,5-methylene-thiopropylene-pyrrolidine-2,4-dione and methanesulphonyl chloride are used as starting material, the course of the reaction can be represented by the following equation:

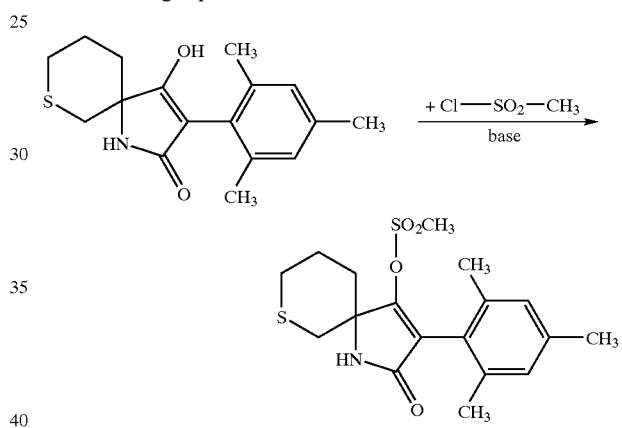

If, in accordance with process (F), 3-(2,4-dimethylphenyl)-5,5-ethylene-thioethylene-pyrrolidine-2,4-dione and 2,2,2-trifluoroethyl chloromethanethiophosphonate are used as starting materials, the course of the reaction can be represented by the following equation:

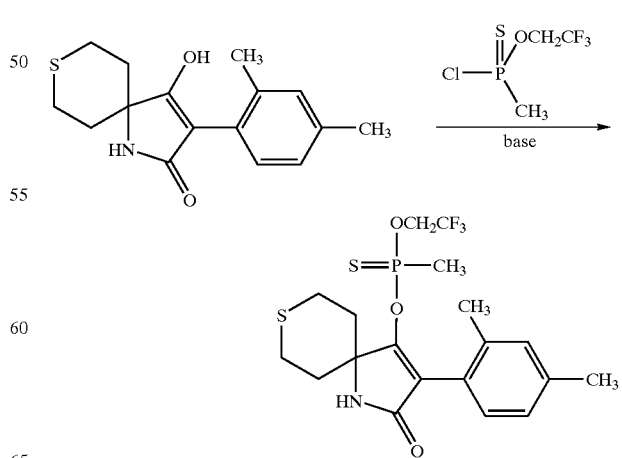

If, in accordance with process (G), 3-(2,4,6-trimethylphenyl)-5,5-ethylene-thiomethylene-pyrrolidine-2,4-dione and NaOH are used as components, the course of the process according to the invention can be represented by the following equation:

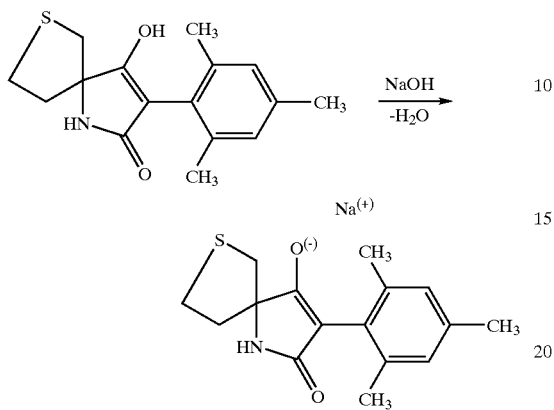

If, in accordance with process ($H_a$), 3-(2,4,-trimethylphenyl)-5,5-ethyleneoxaethylene-pyrrolidine-2,4-dione and ethyl isocyanate are used as starting materials, the course of the reaction can be represented by the following equation:

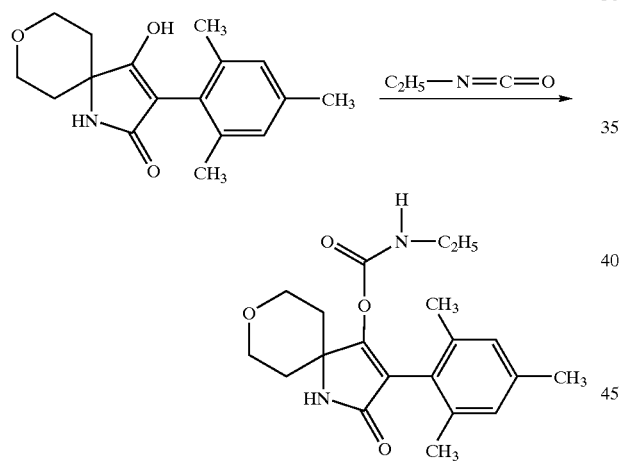

If, in accordance with process ($H_b$), 3-(2,4,6-trimethylphenyl)-5,5-(ethylenebenzylamino-ethylene-pyrrolidine-2,4-dione and dimethylcarbamoyl chloride are used as starting materials, the course of the reaction can be represented by the following equation:

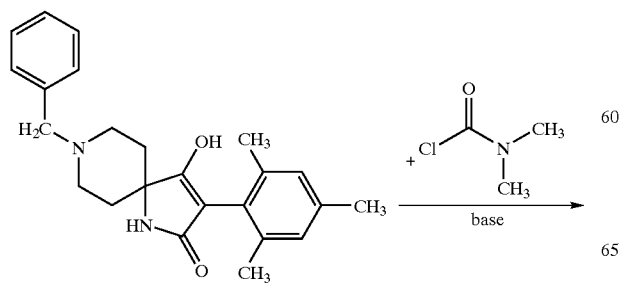

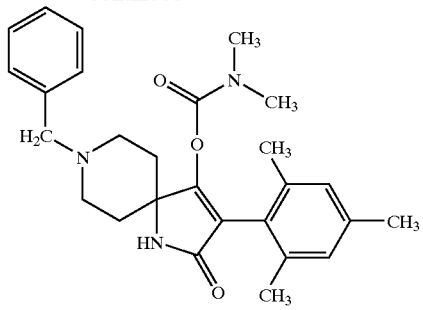

The cyclic aminocarboxylic acids which are interrupted by hetero atoms, of the formula (XIVa), in which A and B have the abovementioned meaning, can generally be obtained by means of a Bucherer-Bergs reaction or a Strecker synthesis.

(XIVa)

(L. Munday, J. Chem. Soc. 4372 (1961); J. T. Eward, C. Jitrangeri, Can. J. Chem. 53, 3339 (1975).

Furthermore, the starting materials of the formula (II)

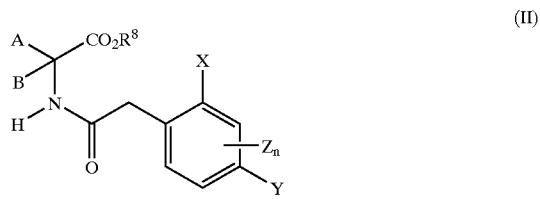
(II)

in which

A, B, X, Y, Z, n and $R^8$ have the abovementioned meaning and which are used in the above processes (A) can be prepared when aminonitriles of the formula (XVI)

(XVI)

in which

A and B have the abovementioned meaning, are reacted with phenylacetyl halides of the formula (XV)

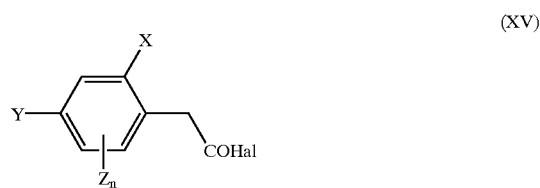
(XV)

in which

X, Y, Z and n have the abovementioned meaning and Hal represents chlorine or bromine to give compounds of the formula (XVI)

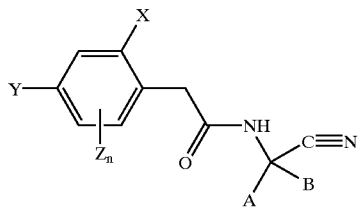
(XVII)

in which
A, B, X, Y, Z and n have the abovementioned meaning,
which are subsequently subjected to alcoholysis in sulphuric acid.

The compounds of the formula (XVII) are also new and are the subject-matter of the general claim of an earlier application, which also includes the processes.

The compounds of the formula (II)

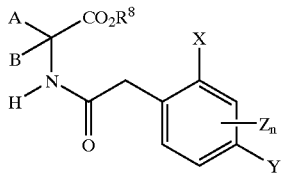
(II)

in which
A, B, X, Y, Z, n and $R^8$ have the abovementioned meaning,
and which are required as starting materials in the above process (A) are new and are the subject-matter of the general claim of an earlier application.

For example, acyl-amino acid esters of the formula (II) are also obtained when amino acid derivatives of the formula (XIV)

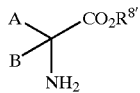
(XIV)

in which
$R^{8'}$ represents hydrogen (XIVa) or alkyl (XIVb) and
A and B have the abovementioned meaning
are acylated with phenylacetyl halides of the formula (XV)

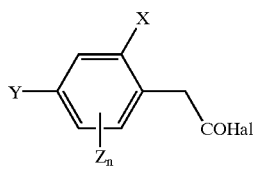
(XV)

in which
X, Y, Z and n have the abovementioned meaning and
Hal represents chlorine or bromine,
(Chem. Reviews 5, 237–416 (1953); Bhattacharya, Indian J. Chem. 6, 341–5, 1968)

and the acylamino acids of the formula (IIa)

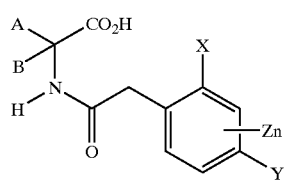
(IIa)

in which
A, B, Y, Z and n have the abovementioned meaning,
which have been formed if $R^{8'}$=hydrogen are esterified.

In addition to the intermediates mentioned in the preparation examples, the following compounds of the formula (II) may be mentioned by way of example, but not by limitation:

methyl N-(2,4-dichlorophenylacetyl)-1-amino-thiolane-carboxylate, methyl N-(2,4-dichlorophenylacetyl)-1-amino-tetrahydrothiopyran-carboxylate, methyl N-(2,4-dichlorophenylacetyl)-1-amino-tetrahydropyran-carboxylate, methyl 4-(2,4-dichlorophenylacetylamino)-N-methyl-piperidine-carboxylate, methyl 4-(2,4-dichlorophenylacetylamino)-N-acetyl-piperidine-carboxylate, methyl 4-(2,4-dichlorophenylacetylamino)-N-carboxyethyl-piperidine-carboxylate, methyl N-(2,6-dichlorophenylacetyl)-1-amino-thiolane-carboxylate, methyl N-(2,6-dichlorophenylacetyl)-1-amino-tetrahydrothiopyran-carboxylate, methyl N-(2,6-dichlorophenylacetyl)-1-amino-tetrahydropyran-carboxylate, methyl 4-(2,6-dichlorophenylacetylamino)-N-methyl-piperidine-4-carboxylate, methyl 4-(2,6-dichlorophenylacetylamino)-N-acetyl-piperidine-4-carboxylate, methyl 4-(2,6-dichlorophenylacetylamino)-N-carboxyethyl-piperidine-4-carboxylate, methyl N-(2-chloro-6-fluoro-phenyl-acetyl)-1-amino-3-thiolane-carboxylate, methyl N-(2-chloro-6-fluoro-phenyl-acetyl)-1-amino-4-tetrahydrothiopyran-carboxylate, methyl N-(2-chloro-6-fluoro-phenyl-acetyl)-1-amino-tetrahydropyran-carboxylate, methyl 4-(2-chloro-6-fluoro-phenyl-acetylamino)-N-methyl-piperidine-4-carboxylate, methyl 4-(2-chloro-6-fluoro-phenyl-acetylamino)-N-acetyl-piperidine-4-carboxylate, methyl 4-(2-chloro-6-fluoro-phenyl-acetylamino)-N-carboxyethyl-piperidine-4-carboxylate, methyl N-(2,4,6-trimethylphenyl-acetyl)-1-amino-thiolane-carboxylate, methyl N-(2,4,6-trimethylphenyl-acetyl)-1-amino-tetrahydrothiopyrancarboxylate, methyl N-(2,4,6-trimethylphenyl-acetyl)-1-amino-tetrahydropyrancarboxylate, methyl 4-(2,4,6-trimethylphenyl-acetylamino)-N-methyl-piperidine-4-carboxylate, methyl (2,4,6-trimethylphenyl-acetylamino)-N-acetyl-piperidine-4-carboxylate, methyl (2,4,6-trimethylphenyl-acetylamino)-N-carboxyethyl-piperidine-4-carboxylate,
methyl N-(2,4-dimethylphenyl-acetyl)-1-amino-thiolane-carboxylate,
methyl N-(2,4-dimethylphenyl-acetyl)-1-amino-tetrahydrothiopyran-carboxylate,
methyl (2,4-dimethylphenyl-acetyl)-1-amino-tetrahydropyran-carboxylate,
methyl 4-(2,4-dimethylphenyl-acetylamino)-N-methyl-piperidine-4-carboxylate,
methyl (2,4-dimethylphenyl-acetylamino)-N-acetyl-piperidine-4-carboxylate,
methyl 4-(2,4-dimethylphenyl-acetylamino)-4-carboxyethyl-piperidine-4-carboxylate,
methyl N-(2,4-dimethylphenyl-acetyl)-1-amino-4-phenyl-cyclohexane-carboxylate.

In addition to the intermediates mentioned in the preparation examples, the following compounds of the formula (IIa) may be mentioned by way of example, but not by limitation:

N-(2,4-dichlorophenylacetyl)-1-amino-thiolane-carboxylic acid,
N-(2,4-dichlorophenylacetyl)-1-amino-tetrahydrothiopyran-carboxylic acid,
N-(2,4-dichlorophenylacetyl)-1-amino-tetrahydropyran-carboxylic acid,
4-(2,4-dichlorophenylacetylamino)-N-methyl-piperidine-4-carboxylic acid,
4-(2,4-dichlorophenylacetylamino)-N-acetyl-piperidine-4-carboxylic acid,
4-(2,4-dichlorophenylacetylamino)-N-carboxyethyl-piperidine-4-carboxylic acid,
N-(2,6-dichlorophenylacetyl)-1-amino-thiolane-carboxylic acid,
N-(2,6-dichlorophenylacetyl)-1-amino-tetrahydrothiopyran-carboxylic acid,
N-(2,6-dichlorophenylacetyl)-1-amino-tetrahydropyran-carboxylic acid,
4-(2,6-dichlorophenylacetylamino)-N-methyl-piperidine-4-carboxylic acid,
4-(2,6-dichlorophenylacetylamino)-N-acetyl-piperidine-4-carboxylic acid,
4-(2,6-dichlorophenylacetylamino)-N-carboxyethyl-piperidine-4-carboxylic acid,
N-(2-chloro-6-fluoro-phenyl-acetyl)-1-amino-thiolane-carboxylic acid,
N-(2-chloro-6-fluoro-phenyl-acetyl)-1-amino-tetrahydrothiopyran-carboxylic acid,
N-(2-chloro-6-fluoro-phenyl-acetyl)-1-amino-tetrahydropyran-carboxylic acid,
4-(2-chloro-6-fluoro-phenyl-acetylamino)-N-methyl-piperidine-4-carboxylic acid,
4-(2-chloro-6-fluoro-phenyl-acetylamino)-N-acetyl-piperidine-4-carboxylic acid,
4-(2-chloro-6-fluoro-phenyl-acetylamino)-N-carboxyethyl-piperidine-4-carboxylic acid,
N-(2,4,6-triethylphenyl-acetyl)-1-amino-thiolane-carboxylic acid,
N-(2,4,6-trimethylphenyl-acetyl)-1-amino-tetrahydrothiopyran-carboxylic acid,
N-(2,4,6-trimethylphenyl-acetyl)-1-amino-tetrahydropyran-carboxylic acid,
4-(2,4,6-trimethylphenyl-acetylamino)-N-methyl-piperidine-4-carboxylic acid,
4-(2,4,6-trimethylphenyl-acetylamino)-N-acetyl-piperidine-4-carboxylic acid,
4-(2,4,6-trimethylphenyl-acetylamino)-N-carboxyethyl-piperidine-4-carboxylic acid,
N-(2,4-dimethylphenyl-acetyl)-1-amino-thiolane-carboxylic acid,
N-(2,4-dimethylphenyl-acetyl)-1-amino-tetrahydrothiopyran-carboxylic acid,
N-(2,4-dimethylphenyl-acetyl)-1-amino-tetrahydropyran-carboxylic acid,
4-(2,4-dimethylphenyl-acetylamino)-N-methyl-piperidine-4-carboxylic acid,
4-(2,4-dimethylphenyl-acetylamino)-N-acetyl-piperidine-4-carboxylic acid,
4-(2,4-dimethylphenyl-acetylamino)-N-carboxyethyl-piperidine-4-carboxylic acid.

In addition to the intermediates mentioned in the preparation examples, the following compounds of the formula (XVII) may be mentioned by way of example, but not by limitation:

N-(2,4-dichlorophenylacetyl)-1-amino-thiolane-carbonitrile,
N-(2,4-dichlorophenylacetyl)-1-amino-tetrahydrothiopyran-carbonitrile,
N-(2,4-dichlorophenylacetyl)-1-amino-tetrahydropyran-carbonitrile,
4-(2,4-dichlorophenylacetylamino)-N-methyl-piperidine-4-carbonitrile,
4-(2,4-dichlorophenylacetylamino)-N-acetyl-piperidine-4-carbonitrile,
4-(2,4-dichlorophenylacetylamino)-N-carboxyethyl-piperidine-4-carbonitrile,
N-(2,6-dichlorophenylacetyl)-1-amino-thiolane-carbonitrile,
N-(2,6-dichlorophenylacetyl)-1-amino-tetrahydrothiopyran-carbonitrile,
N-(2,6-dichlorophenylacetyl)-1-amino-tetrahydropyran-carbonitrile,
4-(2,6-dichlorophenylacetylamino)-N-methyl-piperidine-4-carbonitrile,
4-(2,6-dichlorophenylacetylamino)-N-acetyl-piperidine-4-carbonitrile,
4-(2,6-dichlorophenylacetylamino)-N-carboxyethyl-piperidine-4-carbonitrile,
N-(2-chloro-6-fluoro-phenyl-acetyl)-1-amino-thiolane-carbonitrile,
N-(2-chloro-6-fluoro-phenyl-acetyl)-1-amino-tetrahydrothiopyran-carbonitrile,
N-(2-chloro-6-fluoro-phenyl-acetyl)-1-amino-tetrahydropyran-carbonitrile,
4-(2-chloro-6-fluoro-phenyl-acetylamino)-N-methylpiperidine-4-carbonitrile,
4-(2-chloro-6-fluoro-phenyl-acetylamino)-N-acetylpiperidine-4-carbonitrile,
4-(2-chloro-6-fluoro-phenyl-acetylamino)-N-carboxyethyl-piperidine-4-carbonitrile,
N-(2,4,6-trimethylphenyl-acetyl)-1-amino-thiolane-carbonitrile,
N-(2,4,6-trimethylphenyl-acetyl)-1-amino-tetrahydrothiopyran-carbonitrile, N-(2,4,6-trimethylphenyl-acetyl)-1-amino-tetrahydropyrancarbonitrile, 4-(2,4,6-trimethylphenyl-acetylamino)-N-methyl-piperidinen-4-carbonitrile, 4-(2,4,6-trimethylphenyl-acetylamino)-N-acetyl-piperidine-4-carbonitrile, 4-(2,4,6-trimethylphenyl-acetylamino)-N-carboxyethyl-piperidine-4-carbonitrile, N-(2,4-dimethylphenyl-acetyl)-1-amino-thiolane-carbonitrile, N-(2,4-dimethylphenyl-acetyl)-1-amino-tetrahydrothiopyran-carbonitrile, N-(2,4-dimethylphenyl-acetyl)-1-amino-tetrahydropyran-carbonitrile, 4-(2,4-dimethylphenyl-acetylamino)-N-methyl-piperidine-4-carbonitrile, 4-(2,4-dimethylphenyl-acetylamino)-N-acetyl-piperidine-4-carbonitrile, 4-(2,4-dimethylphenyl-acetylamino)-N-carboxyethyl-piperidine-4-carbonitrile.

Compounds of the formula (IIa) can be obtained, for example, from the phenylacetyl halides of the formula (XV) and amino acids of the formula (XIVa) by the method of Schotten-Baumann (Organikum [Laboratory Practical of Organic Chemistry], 9th Edition, 446 (1970) VEB Deutscher Verlag der Wissenschaften, Berlin).

The acid halides of the formula (III), carboxylic anhydrides of the formula (IV), chloroformic esters or chloroformic thioesters of the formula (V), chloromonothioformic esters or chlorodithioformic esters of the formula (VI), alkyl halides of the formula (VII), sulphonyl chlorides of the formula (VIII), phosphorus compounds of the formula (IX) and metal hydroxides or amines of the formula (X) and (XI) and isocyanates of the formula (XII) or carbamoyl chloride of the formula (XIII), which are furthermore required as starting materials for carrying out processes (B), (C), (D), (E), (F), (G) and (H) according to the invention are generally known compounds of organic or inorganic chemistry.

Process (A) is characterized in that compounds of the formula (II) in which A, B, X, Y, Z, n and $R^8$ have the abovementioned meaning are subjected to an intramolecular condensation reaction in the presence of bases.

Diluents which can be employed in process (A) according to the invention are all inert organic solvents. The following can preferably be used: hydrocarbons such as toluene and xylene, furthermore ethers such as dibutyl ether, tetrahydrofuran, dioxane, glycol dimethyl ether and diglycol dimethyl ether, furthermore polar solvents such as dimethyl sulphoxide, sulpholane, dimethylforamide and N-methyl-pyrrolidone, and also alcohols such as methanol, ethanol, propanol, isopropanol, butanol, iso-butanol and tert-butanol.

Bases (deprotonating agents) which can be employed when carrying out process (A) according to the invention are all customary proton acceptors. The following can preferably be used: the oxides, hydroxides and carbonates of alkali metals and alkaline earth metals such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammoniun bromide, ®Adogen 464 or TDA 1*).

Adogen 464=methyltrialkyl($C_8$–$C_{10}$)ammonium chloride
TDA 1=tris-(methoxyethoxyethyl)-amine Furthermore, alkali metals such as sodium or potassium can be used. Other substances which can be employed are alkali metal amides, alkali metal hydrides, alkaline earth metal amides and alkaline earth metal hydrides, such as sodium amide, sodium hydride and calcium hydride, and furthermore also alkali metal alcoholates, such as sodium methylate, sodium ethylate and potassium tert-butylate.

When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formulae (II) and the deprotonating bases are generally employed in approximately twice the molar amount. However, it is also possible to use a larger excess (up to 3 mol) of one or the other component.

Process (Bα) is character in that compounds of the formula (Ia) are reacted with carboxylic acid halides of the formula (III).

When using the acid halides, diluents which can be employed in process (Ba) according to the invention are all solvents which are inert towards these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, furthermore ketones such as acetone and methyl isopropyl ketone, moreover ethers, such as diethyl ether, tetrahydrofuran and dioxane, in addition carboxylic esters, such as ethyl acetate, and also strongly polar solvents such as dimethyl sulphoxide and sulpholane. If the acid halide is sufficiently stable to hydrolysis, the reaction may also be carried out in the presence of water.

If the corresponding carboxylic acid halides are used, then suitable acid-binding agents in the reaction of process (Bα) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides such as magnesium oxide and calcium oxide, moreover alkali metal carbonates and alkaline earth metal carbonates, such as sodium carbonate, potassium carbonate and calcium carbonate, and also alkali metal hydroxides such as sodium hydroxide and potassium hydroxide.

When using carboxylic acid halides in process (Bα) according to the invention, the reaction temperatures can also be varied within a substantial range. In general, the process is carried out at temperatures between –20° C. and +150° C., preferably between 0° C. and 100° C.

When carrying out process (Bα) according to the invention, the starting materials of the formula (Ia) and the carboxylic acid halide of the formula (III) are generally used in approximately equivalent amounts. However, it is also possible to use a larger excess (up to 5 mol) of the carboxylic acid halide. Working-up is carried out by customary methods.

Process (Bβ) is characterized in that compounds of the formula (Ia) are reacted with carboxylic anhydrides of the formula (IV).

If carboxylic anhydrides are used as reactant of the formula (IV) in process (Bβ) according to the invention, then diluents which can be used are preferably those which are also preferably suitable when acid halides are used. In addition, an excess of carboxylic anhydride employed may also simultaneously act as the diluent.

When using carboxylic anhydrides in process (Bβ) according to the invention, the reaction temperatures can be varied within a substantial range. In general, the process is carried out at temperatures between −20° C. and +150° C., preferably between 0° C. and 100° C.

When carrying out the process according to the invention, the starting materials of the formula (Ia) and the carboxylic anhydride of the formula (IV) are generally used in approximately equivalent amounts. However, it is also possible to use a larger excess (up to 5 mol) of the carboxylic acid halide. Working-up is carried out by customary methods.

In general, a procedure is followed in which diluent, the excess of carboxylic anhydride and the carboxylic acid which is formed are removed by distillation or by washing with an organic solvent or with water.

Process (C) is characterized in that compounds of the formula (Ia) are reacted with chloroformic esters or chloroformic thiolesters of the formula (V).

If the corresponding chloroformic esters or chloroformic thiolesters are used, then suitable acid-binding agents for the reaction in accordance with process (C) according to the invention are all customary acid acceptors. The following can preferably be used: tertiary amines such as triethylamine, pyridine, DABCO, DBU, DBA, Hünig base and N,N-dimethyl-aniline, furthermore alkaline earth metal oxides such as magnesium oxide and calcium oxide, in addition alkali metal carbonates and alkaline earth metal carbonates, such as sodium carbonate, potassium carbonate and calcium carbonate, and also alkali metal hydroxides such as sodium hydroxide and potassium hydroxide.

When using the chloroformic esters or chloroformic thiolesters in process (C) according to the invention, suitable diluents are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylic esters, such as ethyl acetate, and also strongly polar solvents, such as dimethyl sulphoxide and sulpholane.

When using the chloroformic esters or chloroformic thiolesters as carboxylic acid derivatives of the formula (V), the reaction tempt for carrying out process (C) according to the invention can be varied within a substantial range. If the process is carried out in the presence of a diluent and of an acid-binding agent, the reaction temperatures are generally between −20° C. and +100° C., preferably between 0° C. and 50° C.

Process (C) according to the invention is generally carried out under atmospheric pressure.

When carrying out process (C) according to the invention, the starting materials of the formula (Ia) and the corresponding chloroformic ester or chloroformic thiolester of the formula (V) are generally employed in approximately equivalent amounts. However, it is also possible to employ a larger excess (up to 2 mol) of one or the other component. Working-up is then carried out by customary methods. In general, a procedure is followed in which precipitated salts are removed and the reaction mixture which remains is concentrated by stripping off the diluent.

In preparation process (D), approximately 1 mol of chloromonothioformic ester or chlorodithioformic ester of the formula (VI) is reacted per mole of starting compound of the formula (Ia) at 0 to 120° C., preferably at 20 to 60° C.

Suitable diluents which are optionally added are all inert polar organic solvents, such as ethers, amides, alcohols, sulphones and sulphoxides.

Dimethyl sulphoxide, tetrahydrofuran, dimethylforamide and dimethyl sulphide are preferably employed.

If, in a preferred embodiment, the enolate salt of the compound Ia is synthesized by adding strong deprotonating agents such as, for example, sodium hydride or potassium tertiary butylate, a further addition of acid-binding agent can be dispensed with.

If acid-binding agents are employed, then suitable substances are customary inorganic or organic bases, with sodium hydroxide, sodium carbonate, potassium carbonate, pyridine and triethylamine being mentioned as examples.

The reaction can be carried out under atmospheric pressure or under elevated pressure, preferably under atmospheric pressure. Working-up is carried out by customary methods.

In preparation process (D$_\beta$), the equimolar amount or an excess of carbon disulphide is added per mole of starting compound of the formula (Ia).

This process is preferably carried out at temperatures from 0 to 50° C. and in particular from 20 to 30° C.

It is frequently expedient to first prepare the corresponding salt from the compound of the formula (Ia) by adding a deprotonating agent (such as, for example, potassium tertiary-butylate or sodium hydride). The compound (Ia) is reacted with carbon disulphide until the formation of the intermediate is complete, for example after stirring at room temperature for several hours.

The further reaction with the alkyl halide of the formula (VII) is preferably carried out at 0 to 70° C. and in particular at 20 to 50° C. At least the equimolar amount of alkyl halide is employed for this purpose.

The process is carried out under atmospheric pressure or under elevated pressure, preferably under atmospheric pressure.

Again, working-up is carried out by customary methods.

In preparation process (E), approximately 1 mol of sulphonyl chloride (VIII) is reacted per mole of starting compound of the formula (Ia) at 0 to 150° C., preferably at 20 to 70° C.

Suitable diluents which are optionally added are all inert polar organic solvents such as ethers, aimides, nitriles, alcohols, sulphones, sulphoxides or halogenated hydrocarbons such as methylene chloride.

Dimethyl sulphoxide, tetrahydrofuran, dimethylforamide, dimethyl sulphide and methylene chloride are preferably employed.

If, in a preferred embodiment, the enolate salt of the compound Ia is synthesized by adding strong deprotonating agents (such as, for example, sodium hydride or potassium tertiary-butylate), a further addition of acid-binding agent can be dispensed with.

If acid-binding agents are employed then suitable substances are customary inorganic or organic bases, with sodium hydroxide, sodium carbonate, potassium carbonate and pyridine being mentioned as examples.

The reaction can be carried out under atmospheric pressure or under elevated pressure, preferably under atmospheric pressure. Working-up is carried out by customary methods.

Preparation process (E) can optionally be carried out under phase transfer conditions (W. J. Süillane et al.; J. Chem. Soc., Perkin Trans I, (3) 677–9 (1982)). In this case, 0.3 to 1.5 mol of sulphonyl chloride VIII, preferably 0.5 mol, are reacted per mole of starting compound of the formula (Ia) at 0° to 150° C., preferably at 20 to 70° C.

Phase transfer catalysts which can be used are all quaternary ammonium salts, preferably tetraoctylammonium bromide and benzyltriethylammonium chloride. In this case, all non-polar inert solvents may act as organic solvents; benzene and toluene are preferably employed.

To obtain compounds of the structure (Ie) in preparation process (F), 1 to 2, preferably 1 to 1.3, mol of the phosphorus compound of the formula (IX) are reacted per mole of the compound (Ia) at temperature between −40° C. and 150° C., preferably between −10 and 110° C.

Suitable diluents which are optionally added are all inert polar organic solvents such as ethers, amides, nitrites, alcohols, sulphides, sulphones, sulphoxides and the like.

Acetonitrile, dimethyl sulphoxide, tetrahydrofuran, dimethylforamide or dimethyl sulphide are preferably employed.

Suitable acid-binding agents which are optionally added are customary inorganic or organic bases such as hydroxides or carbonates. Examples which may be mentioned are sodium hydroxide, sodium carbonate, potassium carbonate and pyridine.

The reaction can be carried out under atmospheric pressure or under elevated pressure, preferably under atmospheric pressure. Working-up is carried out by customary methods of organic chemistry. The end products obtained are preferably purified by crystallization, chromatographic purification or by so-called "incipient distillation", i.e. removal of the volatile components in vacuo.

Process (G) is characterized in that compounds of the formula (Ia) are reacted with metal compounds (X) or amines (XI).

Diluents which can be employed in the process according to the invention are preferably ethers such as tetrahydrofuran, dioxane, diethyl ether, or else alcohols such as methanol, ethanol and isopropanol, but also water. The process (G) according to the invention is generally carried out under atmospheric pressure. The reaction temperatures are generally between −20° C. and 100° C., preferably between 0° C. and 50° C.

In preparation process (Hα), approximately 1 mol of isocyanate of the formula (XII) is reacted per mole of starting compound of the formula (Iα) at 0 to 100° C., preferably at 20 to 50° C.

Suitable diluents which are optionally added are all inert organic solvents such as ethers, amides, nitrites, sulphones and sulphoxides.

If appropriate, catalysts may be added to accelerate the reaction. Catalysts which are very advantageously employed are organotin compounds such as, for example, dibutyltin dilaurate. The process is preferably carried out under atmospheric pressure.

In preparation process (Hβ), approximately 1 mol of carbamoyl chloride of the formula (XIII) is reacted per mole of starting compound of the formula (Ia) at 0 to 150° C., preferably at 20 to 70° C.

Suitable diluents which are optionally added are all inert polar organic solvents such as ethers, amides, alcohols, sulphones or sulphoxides.

Dimethyl sulphoxide, tetrahydrofuran, dimethylforamide or methylene chloride are preferably employed.

If, in a preferred embodiment, the enolate salt of the compound (Ia) is synthesized by adding strong deprotonating agents (such as, for example, sodium hydride or potassium tertiary-butylate), a further addition of acid-binding agents can be dispensed with.

If acid-binding agents are employed, then suitable substances are customary inorganic or organic bases, with sodium hydroxide, sodium carbonate, potassium carbonate, triethylamine or pyridine being mentioned as examples.

The reaction can be carried out under atmospheric pressure or under elevated pressure, preferably under atmospheric pressure. Working-up is carried out by customary methods.

The active compounds are suitable for combating animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella imnmaculata.*

From the order of the Thysanura, for example, *Lepisma saccharin.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria nigratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pel-*

*lionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis, Anthonomus* spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., *Cono derus* spp., *Melolontha melolontha, Amphimallon solsti tialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocehala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a powerful insecticidal and acaricidal activity.

They can be employed particularly successfully for combating insects which damage plants, for example against the larvae of the mustard beetle (*Phaedon cochleariae*) or against the larvae of the green rice leafhopper (*Nephotettix cincticeps*) for combating mites which damage plants, such as, for example, the greenhouse red spider mite or the two-spotted spider mite (*Tetranychus urticae*).

The active compounds according to the invention can furthermore be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lmmium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecrus and Apera.

Monocotyledon cultures of the genera: Oryza, Zea, Triticum, Hordeum, Avena, Secale, Sorghurm, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds according to the invention are highly suitable for selectively combating monocotyledon weeds in dicotyledon cultures by the pre- and post-emergence methods. For example, they can be used very successfully in cotton or sugar beet for combating grass weeds.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or pare, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montrnorillonite or diatornaceous earth and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligrin-sulphite waste liquors and methylcellulose.

Adhesives such as carboxymethylcellulose and natural and synthetic polymers in the form of powders, granules or latexes, such as gun arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and t nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as a with known herbicides, finished formulations or tank mixes being possible.

Suitable herbicides for the mixtures are known herbicides, such as, for example, 1-amino-6-ethylthio-3-(2,2-dimethyl-propyl)-1,3,5-triazine-2,4(1H,3H)dione (AMETHYDIONE) or N-(2-benzothiazolyl)-N,N'-dimethylurea (META-BENZTHIAZURON) for combating weeds in cereals; 4-amino-3-methyl-6-phenyl-1,2,4-triazin-5(4H)one (METAMITRON) for combating weeds in sugar beet and 4-amino-6-(1,1-dimethylethyl)-3-methylthio-1,2,4-triazin-5(4H)one (METRIBUZIN) for combating weeds in soya beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N-[(4-methoxy-6-methyl-1,3,5-triazin-2-yl)-amino]-carbonylbenzenesulphonamide (CHLORSULFURON); 2-[4-(2,4-dichlorophenoxy)-phenoxy]-propionic acid, its methyl ester or its ethyl ester (DICLOFOPMETHYL); 4-amino-6-t-butyl-3-ethylthio-1,2,4-triazin-5(4H)-one (ETHIOZIN); 2-4[(6-chloro-2-benzoxazolyl)oxy]-phenoxy-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (OSOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (FENACED); 2-[[((4-methoxymethyl-1,3,5-triazin-2-ylamino)-carbonyl]-amino]-sulphonyl-benzoic acid or its (METULFURON); N-(1-ethylpropyl)-3,4-dimethyl-2,6-dinitroaniline (PENDIMETHALIN); 0-(6-chloro-3-phenyl-pyridazin-4-yl) S-octyl thiocarbonate (PYRIDATE); 4-ethylamino-2-t-butylainomethylthio-s-triazine (TERBUTRYNE); 3-[[[[(4methoxy-6-methyl-1,3,5-triazin-2-yl)-amino]-carbonyl]-amino]-sulphonyl]-thiophene-2-carboxylic acid (THIAION) are also possible. Surprisingly, some mixtures also show a synergistic action.

Mixtures with other known active compounds, such as fungicides, insecticides, acaricides, nematicides, bird repellants, plant nutrients and agents which improve soil structure, are also possible.

The insecticides include, for example, phosphates, carbamates, carboxylates, chlorinated hydrocarbons, phenylureas or substances produced from microorganisms and the like.

The following compounds may be mentioned:
acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenproparin, fenvalerate, flucythrinate, fluvalinate, lambdacyhalothrin, permethrin, pyresmethrin, pyrethrum, silfafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophos, naled, omethoate, oxydemeton M, oxydeprofos, parathion A, parathion M, phenthoate, phorate, phosalone, phosmet, phosphamdon, phoxim, piririphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenruon, triflumuron, imidacloprid, nitenpyram, N-[(6-chloro-3-pyridinyl)methyl]-N'-cyano-N-methylethaneimide (NI-25), abamectin, amitrazin, avermectin, azadirachtin, bensultap, *Bacillus thuringiensis*, cyromazine, diafenthiuron, emamectin, ethofenprox, fenpyrad, fipronil, flufenprox, lufenuron, metaldehyd, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-trifluoromethyl)-1H-pyrrole carbonitrile (AC 303630).

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example Ia-1

49.9 g of potassium t-butylate are introduced into 130 ml of dry tetrahydrofuran, a solution of 65 g of methyl N-(2,4,6-trimethylphenyl)-acetyltetrahydrothiophene-3-aminocarboxylate in 420 ml of dry toluene are added under reflux, and the mixture is refluxed for 90 minutes. After cooling, the reaction solution is treated with 650 ml of water and the aqueous phase is separated off. The organic phase is washed with another 300 ml of water. The aqueous phases are combined and acidified with 70 ml of concentrated hydrochloric acid, and the precipitate is filtered off with suction and dried This gives 56 g (96% of theory), m.p. >230° C.

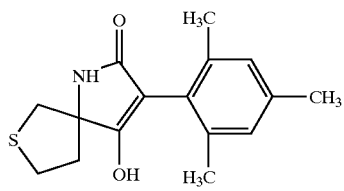

The following compounds are obtained analogously:

TABLE 1a

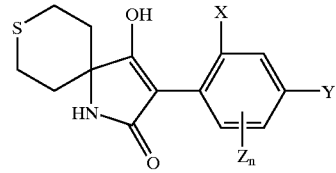

| Ex. No. | X | Y | $Z_n$ | M.p. ° C. |
|---|---|---|---|---|
| Ia-2 | Cl | Cl | H | >220 |
| Ia-3 | Cl | H | 6-F | |
| Ia-4 | Cl | H | 6-Cl | |
| Ia-5 | $CH_3$ | $CH_3$ | H | |
| Ia-6 | Cl | $CF_3$ | 6-Cl | |

TABLE 1b

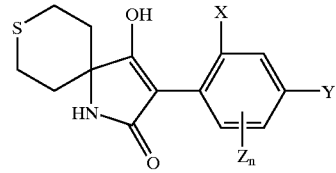

| Ex. No. | X | Y | $Z_n$ | M.p. ° C. |
|---|---|---|---|---|
| Ia-7 | Cl | Cl | H | |
| Ia-8 | Cl | H | 6-F | |
| Ia-9 | Cl | H | 6-Cl | |
| Ia-10 | $CH_3$ | $CH_3$ | H | |
| Ia-11 | $CH_3$ | $CH_3$ | 6-$CH_3$ | >220 |
| Ia-12 | Cl | $CF_3$ | 6-Cl | |

TABLE 1c

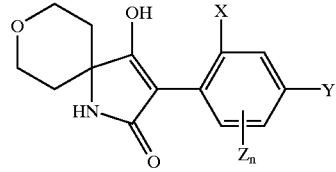

| Ex. No. | X | Y | $Z_n$ | M.p. ° C. |
|---|---|---|---|---|
| Ia-13 | Cl | Cl | H | >220 |
| Ia-14 | Cl | H | 6-F | |
| Ia-15 | Cl | H | 6-Cl | |
| Ia-16 | $CH_3$ | $CH_3$ | H | >230 |
| Ia-17 | $CH_3$ | $CH_3$ | 6-$CH_3$ | >220 |
| Ia-18 | Cl | $CF_3$ | 6-Cl | |

TABLE 1d

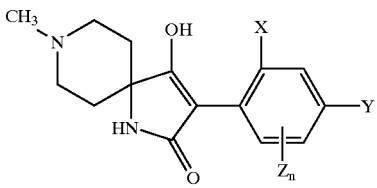

| Ex. No. | X | Y | $Z_n$ | M.p. ° C. |
|---|---|---|---|---|
| Ia-20 | Cl | Cl | H | |
| Ia-21 | Cl | H | 6-F | |
| Ia-22 | Cl | H | 6-Cl | |
| Ia-23 | $CH_3$ | $CH_3$ | H | |
| Ia-24 | $CH_3$ | $CH_3$ | 6-$CH_3$ | >220 |
| Ia-25 | Cl | $CF_3$ | 6-Cl | |

TABLE 1e

| Ex. No. | X | Y | $Z_n$ | M.p. °C. |
|---|---|---|---|---|
| Ia-26 | Cl | Cl | H | |
| Ia-27 | Cl | H | 6-F | |
| Ia-28 | Cl | H | 6-Cl | |
| Ia-29 | $CH_3$ | $CH_3$ | H | |
| Ia-30 | $CH_3$ | $CH_3$ | 6-$CH_3$ | >220 |
| Ia-31 | Cl | $CF_3$ | 6-Cl | |

TABLE 1f

| Ex. No. | X | Y | $Z_n$ | M.p. °C. |
|---|---|---|---|---|
| Ia-32 | Cl | Cl | H | |
| Ia-33 | Cl | H | 6-F | |
| Ia-34 | Cl | H | 6-Cl | |
| Ia-35 | $CH_3$ | $CH_3$ | H | |
| Ia-36 | $CH_3$ | $CH_3$ | 6-$CH_3$ | |
| Ia-37 | Cl | $CF_3$ | 6-Cl | |

Example Ib -1

5.8 g of the compound of Example Ia-1 in 70 ml of dry methylene chloride are treated with 2.8 ml of triethylamine, and 1.5 ml of acetyl chloride in 5 ml of dry methylene chloride are added at 0 to 10° C. The reaction solution is washed twice using 200 ml of 0.5 N sodium hydroxide solution and dried over magnesium sulphate, and the solvent is distilled off. 1.7 g (26% of theory) remain, m.p. 211° C.

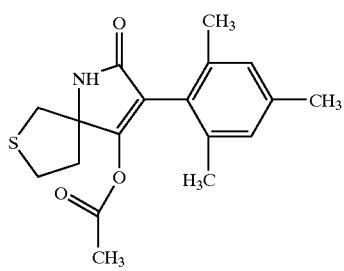

Example I b-1

The following compounds are obtained analogously:

TABLE 2a

| Ex. No. | X | Y | $Z_n$ | $R^1$ | M.p. °C. |
|---|---|---|---|---|---|
| Ib-2 | Cl | Cl | H | $CH_3$ | 199–201 |
| Ib-3 | Cl | H | 6-F | $CH_3$ | |
| Ib-4 | Cl | H | 6-Cl | $CH_3$ | |
| Ib-5 | $CH_3$ | $CH_3$ | H | $CH_3$ | |
| Ib-6 | Cl | $CF_3$ | 6-Cl | $CH_3$ | |
| Ib-7 | Cl | Cl | H | i-$C_3H_7$ | 133–135 |
| Ib-8 | Cl | H | 6-F | i-$C_3H_7$ | |
| Ib-9 | Cl | H | 6-Cl | i-$C_3H_7$ | |
| Ib-10 | $CH_3$ | $CH_3$ | H | i-$C_3H_7$ | |
| Ib-11 | $CH_3$ | $CH_3$ | 6-$CH_3$ | i-$C_3H_7$ | 175 |
| Ib-12 | Cl | $CF_3$ | 6-Cl | i-$C_3H_7$ | |
| Ib-13 | Cl | Cl | H | t-$C_4H_9$ | |
| Ib-14 | Cl | H | 6-F | t-$C_4H_9$ | |
| Ib-15 | Cl | H | 6-Cl | t-$C_4H_9$ | |
| Ib-16 | $CH_3$ | $CH_3$ | H | t-$C_4H_9$ | |
| Ib-17 | $CH_3$ | $CH_3$ | 6-$CH_3$ | t-$C_4H_9$ | 185 |
| Ib-18 | Cl | $CF_3$ | 6-Cl | t-$C_4H_9$ | |
| Ib-19 | Cl | Cl | H | Ph | |
| Ib-20 | Cl | H | 6-F | Ph | |
| Ib-21 | Cl | H | 6-Cl | Ph | |
| Ib-22 | $CH_3$ | $CH_3$ | H | Ph | |
| Ib-23 | $CH_3$ | $CH_3$ | 6-$CH_3$ | Ph | |
| Ib-24 | Cl | $CF_3$ | 6-Cl | Ph | |

TABLE 2b

| Ex. No. | X | Y | $Z_n$ | $R^1$ | M.p. °C. |
|---|---|---|---|---|---|
| Ib-25 | Cl | Cl | H | $CH_3$ | |
| Ib-27 | Cl | H | 6-F | $CH_3$ | |
| Ib-28 | Cl | H | 6-Cl | $CH_3$ | |
| Ib-29 | $CH_3$ | $CH_3$ | H | $CH_3$ | |
| Ib-30 | $CH_3$ | $CH_3$ | 6-$CH_3$ | $CH_3$ | >220 |
| Ib-31 | Cl | $CF_3$ | 6-Cl | $CH_3$ | |
| Ib-32 | Cl | Cl | H | i-$C_3H_7$ | |
| Ib-33 | Cl | H | 6-F | i-$C_3H_7$ | |
| Ib-34 | Cl | H | 6-Cl | i-$C_3H_7$ | |
| Ib-35 | $CH_3$ | $CH_3$ | H | i-$C_3H_7$ | |
| Ib-36 | $CH_3$ | $CH_3$ | 6-$CH_3$ | i-$C_3H_7$ | 208–209 |
| Ib-37 | Cl | $CF_3$ | 6-Cl | i-$C_3H_7$ | |
| Ib-38 | Cl | Cl | H | t-$C_4H_9$ | |
| Ib-39 | Cl | H | 6-F | t-$C_4H_9$ | |
| Ib-40 | Cl | H | 6-Cl | t-$C_4H_9$ | |
| Ib-41 | $CH_3$ | $CH_3$ | H | t-$C_4H_9$ | |
| Ib-42 | $CH_3$ | $CH_3$ | 6-$CH_3$ | t-$C_4H_9$ | >220 |
| Ib-43 | Cl | $CF_3$ | 6-Cl | t-$C_4H_9$ | |
| Ib-44 | Cl | Cl | H | phenyl | |

TABLE 2b-continued

| Ex. No. | X | Y | $Z_n$ | $R^1$ | M.p. ° C. |
|---|---|---|---|---|---|
| Ib-45 | Cl | H | 6-F | phenyl | |
| Ib-46 | Cl | H | 6-Cl | phenyl | |
| Ib-47 | $CH_3$ | $CH_3$ | H | phenyl | |
| Ib-48 | $CH_3$ | $CH_3$ | 6-$CH_3$ | phenyl | |
| Ib-49 | Cl | $CF_3$ | 6-Cl | phenyl | |

TABLE 2c

| Ex. No. | X | Y | $Z_n$ | $R^1$ | M.p. ° C. |
|---|---|---|---|---|---|
| Ib-50 | Cl | Cl | H | $CH_3$ | |
| Ib-51 | Cl | H | 6-F | $CH_3$ | |
| Ib-52 | Cl | H | 6-Cl | $CH_3$ | |
| Ib-53 | $CH_3$ | $CH_3$ | H | $CH_3$ | |
| Ib-54 | $CH_3$ | $CH_3$ | 6-$CH_3$ | $CH_3$ | |
| Ib-55 | Cl | $CF_3$ | 6-Cl | $CH_3$ | |
| Ib-56 | Cl | Cl | H | $i$-$C_3H_7$ | |
| Ib-57 | Cl | H | 6-F | $i$-$C_3H_7$ | |
| Ib-58 | Cl | H | 6-Cl | $i$-$C_3H_7$ | |
| Ib-59 | $CH_3$ | $CH_3$ | H | $i$-$C_3H_7$ | |
| Ib-60 | $CH_3$ | $CH_3$ | 6-$CH_3$ | $i$-$C_3H_7$ | |
| Ib-61 | Cl | $CF_3$ | 6-Cl | $i$-$C_3H_7$ | |
| Ib-62 | Cl | Cl | H | $t$-$C_4H_9$ | |
| Ib-63 | Cl | H | 6-F | $t$-$C_4H_9$ | |
| Ib-64 | Cl | H | 6-Cl | $t$-$C_4H_9$ | |
| Ib-65 | $CH_3$ | $CH_3$ | H | $t$-$C_4H_9$ | |
| Ib-66 | $CH_3$ | $CH_3$ | 6-$CH_3$ | $t$-$C_4H_9$ | |
| Ib-67 | Cl | $CF_3$ | 6-Cl | $t$-$C_4H_9$ | |
| Ib-68 | Cl | Cl | H | phenyl | |
| Ib-69 | Cl | H | 6-F | phenyl | |
| Ib-70 | Cl | H | 6-Cl | phenyl | |
| Ib-71 | $CH_3$ | $CH_3$ | H | phenyl | |
| Ib-72 | $CH_3$ | $CH_3$ | 6-$CH_3$ | phenyl | |
| Ib-73 | Cl | $CF_3$ | 6-Cl | phenyl | |

TABLE 2d

| Ex. No. | X | Y | $Z_n$ | $R^1$ | M.p. ° C. |
|---|---|---|---|---|---|
| Ib-74 | Cl | Cl | H | $CH_3$ | |
| Ib-75 | Cl | H | 6-F | $CH_3$ | |
| Ib-76 | Cl | H | 6-Cl | $CH_3$ | |
| Ib-77 | $CH_3$ | $CH_3$ | H | $CH_3$ | |
| Ib-78 | $CH_3$ | $CH_3$ | 6-$CH_3$ | $CH_3$ | |
| Ib-79 | Cl | $CF_3$ | 6-Cl | $CH_3$ | |
| Ib-80 | Cl | Cl | H | $i$-$C_3H_7$ | |
| Ib-81 | Cl | H | 6-F | $i$-$C_3H_7$ | |
| Ib-82 | Cl | H | 6-Cl | $i$-$C_3H_7$ | |
| Ib-83 | $CH_3$ | $CH_3$ | H | $i$-$C_3H_7$ | |
| Ib-84 | $CH_3$ | $CH_3$ | 6$CH_3$ | $i$-$C_3H_7$ | |
| Ib-85 | Cl | $CF_3$ | 6-Cl | $i$-$C_3H_7$ | |
| Ib-86 | Cl | Cl | H | $t$-$C_4H_9$ | |
| Ib-87 | Cl | H | 6-F | $t$-$C_4H_9$ | |
| Ib-88 | Cl | H | 6-Cl | $t$-$C_4H_9$ | |
| Ib-89 | $CH_3$ | $CH_3$ | H | $t$-$C_4H_9$ | |
| Ib-90 | $CH_3$ | $CH_3$ | 6-$CH_3$ | $t$-$C_4H_9$ | |
| Ib-91 | Cl | $CF_3$ | 6-Cl | $t$-$C_4H_9$ | |
| Ib-92 | Cl | Cl | H | phenyl | |
| Ib-93 | Cl | H | 6-F | phenyl | |
| Ib-94 | Cl | H | 6-Cl | phenyl | |
| Ib-95 | $CH_3$ | $CH_3$ | H | phenyl | |
| Ib-96 | $CH_3$ | $CH_3$ | 6-$CH_3$ | phenyl | |
| Ib-97 | Cl | $CF_3$ | 6-Cl | phenyl | |

TABLE 2e

| Ex. No. | X | Y | $Z_n$ | $R^1$ | M.p. ° C. |
|---|---|---|---|---|---|
| Ib-98 | Cl | Cl | H | $CH_3$ | |
| Ib-99 | Cl | H | 6-F | $CH_3$ | |
| Ib-100 | Cl | H | 6-Cl | $CH_3$ | |
| Ib-101 | $CH_3$ | $CH_3$ | H | $CH_3$ | |
| Ib-102 | $CH_3$ | $CH_3$ | 6-$CH_3$ | $CH_3$ | |
| Ib-103 | Cl | $CF_3$ | 6-Cl | $CH_3$ | |
| Ib-104 | Cl | Cl | H | $i$-$C_3H_7$ | |
| Ib-105 | Cl | H | 6-F | $i$-$C_3H_7$ | |
| Ib-106 | Cl | H | 6-Cl | $i$-$C_3H_7$ | |
| Ib-107 | $CH_3$ | $CH_3$ | H | $i$-$C_3H_7$ | |
| Ib-108 | $CH_3$ | $CH_3$ | 6-$CH_3$ | $i$-$C_3H_7$ | |
| Ib-109 | Cl | $CF_3$ | 6-Cl | $i$-$C_3H_7$ | |
| Ib-110 | Cl | Cl | H | $t$-$C_4H_9$ | |
| Ib-111 | Cl | H | 6-F | $t$-$C_4H_9$ | |
| Ib-112 | Cl | H | 6-Cl | $t$-$C_4H_9$ | |
| Ib-113 | $CH_3$ | $CH_3$ | H | $t$-$C_4H_9$ | |
| Ib-114 | $CH_3$ | $CH_3$ | 6-$CH_3$ | $t$-$C_4H_9$ | |

TABLE 2e-continued

| Ex. No. | X | Y | $Z_n$ | $R^1$ | M.p. °C. |
|---|---|---|---|---|---|
| Ib-115 | Cl | $CF_3$ | 6-Cl | $t\text{-}C_4H_9$ | |
| Ib-116 | Cl | Cl | H | phenyl | |
| Ib-117 | Cl | H | 6-F | phenyl | |
| Ib-118 | Cl | H | 6-Cl | phenyl | |
| Ib-119 | $CH_3$ | $CH_3$ | H | phenyl | |
| Ib-120 | $CH_3$ | $CH_3$ | 6-$CH_3$ | phenyl | |
| Ib-121 | Cl | $CF_3$ | 6-Cl | phenyl | |

TABLE 2f

| Ex. No. | X | Y | $Z_n$ | $R^1$ | M.p. °C. |
|---|---|---|---|---|---|
| Ib-122 | Cl | Cl | H | $CH_3$ | >220 |
| Ib-123 | Cl | H | 6-F | $CH_3$ | |
| Ib-124 | Cl | H | 6-Cl | $CH_3$ | |
| Ib-125 | $CH_3$ | $CH_3$ | H | $CH_3$ | 186 |
| Ib-126 | $CH_3$ | $CH_3$ | 6-$CH_3$ | $CH_3$ | >220 |
| Ib-127 | Cl | $CF_3$ | 6-Cl | $CH_3$ | |
| Ib-128 | Cl | Cl | H | $i\text{-}C_3H_7$ | 205–206 |
| Ib-129 | Cl | H | 6-F | $i\text{-}C_3H_7$ | |
| Ib-130 | Cl | H | 6-Cl | $i\text{-}C_3H_7$ | |
| Ib-131 | $CH_3$ | $CH_3$ | H | $i\text{-}C_3H_7$ | 169 |
| Ib-132 | $CH_3$ | $CH_3$ | 6-$CH_3$ | $i\text{-}C_3H_7$ | 212–215 |
| Ib-133 | Cl | $CF_3$ | 6-Cl | $i\text{-}C_3H_7$ | |
| Ib-134 | Cl | Cl | H | $t\text{-}C_4H_9$ | 209–212 |
| Ib-135 | Cl | H | 6-F | $t\text{-}C_4H_9$ | |
| Ib-136 | Cl | H | 6-Cl | $t\text{-}C_4H_9$ | |
| Ib-137 | $CH_3$ | $CH_3$ | H | $t\text{-}C_4H_9$ | 162 |
| Ib-138 | $CH_3$ | $CH_3$ | 6-$CH_3$ | $t\text{-}C_4H_9$ | |
| Ib-139 | Cl | $CF_3$ | 6-Cl | $t\text{-}C_4H_9$ | |
| Ib-140 | Cl | Cl | H | Ph | |
| Ib-141 | Cl | H | 6-F | Ph | |
| Ib-142 | Cl | H | 6-Cl | Ph | |
| Ib-143 | $CH_3$ | $CH_3$ | H | Ph | |
| Ib-144 | $CH_3$ | $CH_3$ | 6-$CH_3$ | Ph | |
| Ib-145 | Cl | $CF_3$ | 6-Cl | Ph | |
| Ib-146 | $CH_3$ | $CH_3$ | H | $H_5C_2\text{—}O\text{—}CH_2\text{—}$ | 171 |
| Ib-147 | $CH_3$ | $CH_3$ | H | 4-Cl-phenyl | >220 |
| Ib-148 | $CH_3$ | $CH_3$ | H | 6-Cl-pyridin-3-yl | >220 |
| Ib-149 | $CH_3$ | $CH_3$ | 6-$CH_3$ | $(CH_3)_3C\text{—}CH_2\text{—}$ | 199 |
| Ib-150 | $CH_3$ | $CH_3$ | 6-$CH_3$ | 4-Cl-phenyl | >220 |
| Ib-151 | $CH_3$ | $CH_3$ | 6-$CH_3$ | 6-Cl-pyridin-3-yl | >220 |
| Ib-152 | $CH_3$ | $CH_3$ | 6-$CH_3$ | 2-Cl-3-methylpyridin-3-yl | >220 |
| Ib-153 | $CH_3$ | $CH_3$ | 6-$CH_3$ | thien-2-yl | >220 |
| Ib-154 | $CH_3$ | $CH_3$ | 6-$CH_3$ | cyclopropyl | 201 |
| Ib-155 | $CH_3$ | $CH_3$ | 6-$CH_3$ | $H_5C_2\text{—}O\text{—}CH_2\text{—}$ | 182 |
| Ib-156 | $CH_3$ | $CH_3$ | 6-$CH_3$ | $i\text{-}C_4H_9$ | >220 |
| Ib-157 | $CH_3$ | $CH_3$ | 6-$CH_3$ | fur-2-yl | 214 |

Example Ic-1

5.8 g of the compound of Example Ia-1 in 70 ml of dry methylene chloride are treated with 2.8 ml of triethylamine, and 2.7 g of sec-butyl chloroformate in 5 ml of dry methylene chloride are added at 0 to 10° C. The reaction solution is washed twice using 200 ml of 0.5 N sodium hydroxide solution and dried over magnesium sulphate, and the solvent is distilled off. 1.7 g (22% of theory) remain, m.p. 157° C.

Example I c-1

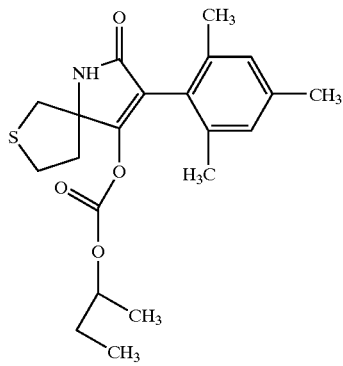

The following compounds are obtained analogously:

TABLE 3a

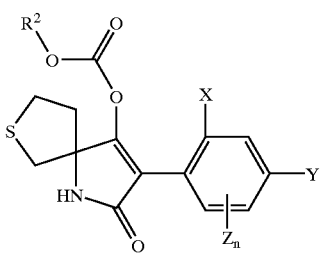

| Ex. No. | X | Y | $Z_n$ | $R^2$ | M.p. °C. |
|---|---|---|---|---|---|
| Ic-2 | Cl | Cl | H | $CH_3$ | |
| Ic-3 | Cl | H | 6-F | $CH_3$ | |
| Ic-4 | Cl | H | 6-Cl | $CH_3$ | |
| Ic-5 | $CH_3$ | $CH_3$ | H | $CH_3$ | |
| Ic-6 | $CH_3$ | $CH_3$ | 6-$CH_3$ | $CH_3$ | |
| Ic-7 | Cl | $CF_3$ | 6-Cl | $CH_3$ | |
| Ic-8 | Cl | Cl | H | $C_2H_5$ | 159–162 |
| Ic-9 | Cl | H | 6-F | $C_2H_5$ | |
| Ic-10 | Cl | H | 6-Cl | $C_2H_5$ | |
| Ic-11 | $CH_3$ | $CH_3$ | H | $C_2H_5$ | |
| Ic-12 | $CH_3$ | $CH_3$ | 6-$CH_3$ | $C_2H_5$ | 134 |
| Ic-13 | Cl | Cl | H | $i$-$C_3H_7$ | |
| Ic-14 | Cl | H | 6-F | $i$-$C_3H_7$ | |
| Ic-15 | Cl | H | 6-Cl | $i$-$C_3H_7$ | |
| Ic-16 | $CH_3$ | $CH_3$ | H | $i$-$C_3H_7$ | |
| Ic-17 | $CH_3$ | $CH_3$ | 6-$CH_3$ | $i$-$C_3H_7$ | |
| Ic-18 | Cl | $CF_3$ | 6-Cl | $i$-$C_3H_7$ | |
| Ic-19 | Cl | Cl | H | $s$-$C_4H_9$ | |
| Ic-20 | Cl | H | 6-F | $s$-$C_4H_9$ | |
| Ic-21 | Cl | H | 6-Cl | $s$-$C_4H_9$ | |
| Ic-22 | $CH_3$ | $CH_3$ | H | $s$-$C_4H_9$ | |
| Ic-23 | Cl | $CF_3$ | 6-Cl | $s$-$C_4H_9$ | |
| Ic-24 | Cl | Cl | H | phenyl | |
| Ic-25 | Cl | H | 6-F | phenyl | |
| Ic-26 | Cl | H | 6-Cl | phenyl | |
| Ic-27 | $CH_3$ | $CH_3$ | H | phenyl | |
| Ic-28 | $CH_3$ | $CH_3$ | 6-$CH_3$ | phenyl | |
| Ic-29 | Cl | $CF_3$ | 6-Cl | phenyl | |
| Ic-30 | Cl | Cl | H | benzyl | |
| Ic-31 | Cl | H | 6-F | benzyl | |
| Ic-32 | Cl | H | 6-Cl | benzyl | |
| Ic-33 | $CH_3$ | $CH_3$ | H | benzyl | |
| Ic-34 | $CH_3$ | $CH_3$ | 6-$CH_3$ | benzyl | |
| Ic-35 | Cl | $CF_3$ | 6-Cl | benzyl | |

TABLE 3b

| Ex. No. | X | Y | $Z_n$ | $R^2$ | M | M.p. °C. |
|---|---|---|---|---|---|---|
| I c-36 | Cl | Cl | H | $i$-$C_3H_7$ | S | |
| I c-37 | Cl | H | 6-F | $i$-$C_3H_7$ | S | |
| I c-38 | Cl | H | 6-Cl | $i$-$C_3H_7$ | S | |
| I c-39 | $CH_3$ | $CH_3$ | H | $i$-$C_3H_7$ | S | |
| I c-40 | $CH_3$ | $CH_3$ | 6-$CH_3$ | $i$-$C_3H_7$ | S | 208–209 |
| I c-41 | Cl | $CF_3$ | 6-Cl | $CH_3$ | O | |
| I c-42 | Cl | Cl | H | $C_2H_5$ | O | |
| I c-43 | Cl | H | 6-F | $C_2H_5$ | O | |
| I c-44 | Cl | H | 6-Cl | $C_2H_5$ | O | |
| I c-45 | $CH_3$ | $CH_3$ | H | $C_2H_5$ | O | |
| I c-46 | $CH_3$ | $CH_3$ | 6-$CH_3$ | $C_2H_5$ | O | 201–202 |
| I c-47 | Cl | Cl | H | $i$-$C_3H_7$ | O | |
| I c-48 | Cl | H | 6-F | $i$-$C_3H_7$ | O | |
| I c-49 | Cl | H | 6-Cl | $i$-$C_3H_7$ | O | |
| I c-50 | $CH_3$ | $CH_3$ | H | $i$-$C_3H_7$ | O | |
| I c-51 | $CH_3$ | $CH_3$ | 6-$CH_3$ | $i$-$C_3H_7$ | O | |
| I c-52 | Cl | $CF_3$ | 6-Cl | $i$-$C_3H_7$ | O | |
| I c-53 | Cl | Cl | H | $s$-$C_4H_9$ | O | |
| I c-54 | Cl | H | 6-F | $s$-$C_4H_9$ | O | |
| I c-55 | Cl | H | 6-Cl | $s$-$C_4H_9$ | O | |
| I c-56 | $CH_3$ | $CH_3$ | H | $s$-$C_4H_9$ | O | |
| I c-57 | $CH_3$ | $CH_3$ | 6-$CH_3$ | $s$-$C_4H_9$ | O | 185–187 |
| I c-58 | Cl | $CF_3$ | 6-Cl | $s$-$C_4H_9$ | O | |
| I c-60 | Cl | Cl | H | phenyl | O | |
| I c-61 | Cl | H | 6-F | phenyl | O | |
| I c-62 | Cl | H | 6-Cl | phenyl | O | |
| I c-63 | $CH_3$ | $CH_3$ | H | phenyl | O | |
| I c-64 | $CH_3$ | $CH_3$ | 6-$CH_3$ | phenyl | O | |
| I c-65 | Cl | $CF_3$ | 6-Cl | phenyl | O | |
| I c-66 | Cl | Cl | H | benzyl | O | |
| I c-67 | Cl | H | 6-F | benzyl | O | |
| I c-68 | Cl | H | 6-Cl | benzyl | O | |
| I c-69 | $CH_3$ | $CH_3$ | H | benzyl | O | |
| I c-70 | $CH_3$ | $CH_3$ | 6-$CH_3$ | benzyl | O | |
| I c-71 | Cl | $CF_3$ | 6-Cl | benzyl | O | |

TABLE 3c

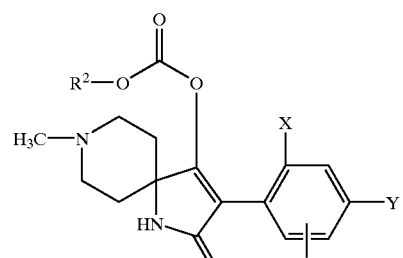

| Ex. No. | X | Y | $Z_n$ | $R^2$ | M.p. °C. |
|---|---|---|---|---|---|
| I c-72 | Cl | Cl | H | $CH_3$ | |
| I c-73 | Cl | H | 6-F | $CH_3$ | |
| I c-74 | Cl | H | 6-Cl | $CH_3$ | |
| I c-75 | $CH_3$ | $CH_3$ | H | $CH_3$ | |
| I c-76 | $CH_3$ | $CH_3$ | 6-$CH_3$ | $CH_3$ | |
| I c-77 | Cl | $CF_3$ | 6-Cl | $CH_3$ | |

TABLE 3c-continued

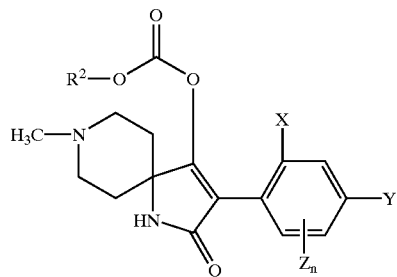

| Ex. No. | X | Y | $Z_n$ | $R^2$ | M.p. °C. |
|---|---|---|---|---|---|
| I c-78 | Cl | Cl | H | $C_2H_5$ | |
| I c-79 | Cl | H | 6-F | $C_2H_5$ | |
| I c-80 | Cl | H | 6-Cl | $C_2H_5$ | |
| I c-81 | $CH_3$ | $CH_3$ | H | $C_2H_5$ | |
| I c-82 | $CH_3$ | $CH_3$ | 6-$CH_3$ | $C_2H_5$ | |
| I c-83 | Cl | Cl | H | $i-C_3H_7$ | |
| I c-84 | Cl | H | 6-F | $i-C_3H_7$ | |
| I c-85 | Cl | H | 6-Cl | $i-C_3H_7$ | |
| I c-86 | $CH_3$ | $CH_3$ | H | $i-C_3H_7$ | |
| I c-87 | $CH_3$ | $CH_3$ | 6-$CH_3$ | $i-C_3H_7$ | |
| I c-88 | Cl | $CF_3$ | 6-Cl | $i-C_3H_7$ | |
| I c-89 | Cl | Cl | H | $s-C_4H_9$ | |
| I c-90 | Cl | H | 6-F | $s-C_4H_9$ | |
| I c-91 | Cl | H | 6-Cl | $s-C_4H_9$ | |
| I c-92 | $CH_3$ | $CH_3$ | H | $s-C_4H_9$ | |
| I c-93 | $CH_3$ | $CH_3$ | 6-$CH_3$ | $s-C_4H_9$ | |
| I c-94 | Cl | $CF_3$ | 6-Cl | $s-C_4H_9$ | |
| I c-95 | Cl | Cl | H | phenyl | |
| I c-96 | Cl | H | 6-F | phenyl | |
| I c-97 | Cl | H | 6-Cl | phenyl | |
| I c-98 | $CH_3$ | $CH_3$ | H | phenyl | |
| I c-99 | $CH_3$ | $CH_3$ | 6-$CH_3$ | phenyl | |
| I c-100 | Cl | $CF_3$ | 6-Cl | phenyl | |
| I c-101 | Cl | Cl | H | benzyl | |
| I c-102 | Cl | H | 6-F | benzyl | |
| I c-103 | Cl | H | 6-Cl | benzyl | |
| I c-104 | $CH_3$ | $CH_3$ | H | benzyl | |
| I c-105 | $CH_3$ | $CH_3$ | 6-$CH_3$ | benzyl | |
| I c-106 | Cl | $CF_3$ | 6-Cl | benzyl | |

TABLE 3d

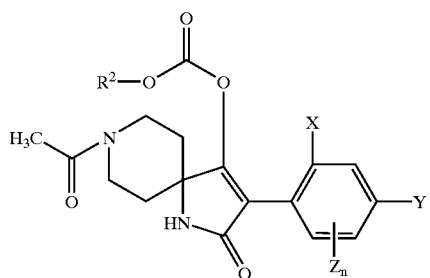

| Ex. No. | X | Y | $Z_n$ | $R^2$ | M.p. °C. |
|---|---|---|---|---|---|
| I c-107 | Cl | Cl | H | $CH_3$ | |
| I c-108 | Cl | H | 6-F | $CH_3$ | |
| I c-109 | Cl | H | 6-Cl | $CH_3$ | |
| I c-110 | $CH_3$ | $CH_3$ | H | $CH_3$ | |
| I c-111 | $CH_3$ | $CH_3$ | 6-$CH_3$ | $CH_3$ | |
| I c-112 | Cl | $CF_3$ | 6-Cl | $CH_3$ | |
| I c-113 | Cl | Cl | H | $C_2H_5$ | |
| I c-114 | Cl | H | 6-F | $C_2H_5$ | |
| I c-115 | Cl | H | 6-Cl | $C_2H_5$ | |
| I c-116 | $CH_3$ | $CH_3$ | H | $C_2H_5$ | |
| I c-117 | $CH_3$ | $CH_3$ | 6-$CH_3$ | $C_2H_5$ | 216 |
| I c-118 | Cl | Cl | H | $i-C_3H_7$ | |

TABLE 3d-continued

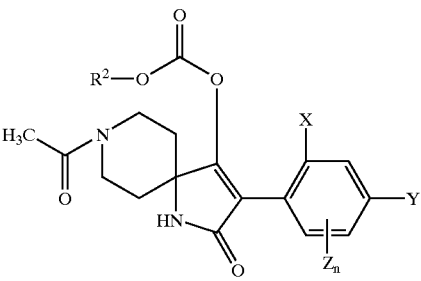

| Ex. No. | X | Y | $Z_n$ | $R^2$ | M.p. °C. |
|---|---|---|---|---|---|
| I c-119 | Cl | H | 6-F | $i-C_3H_7$ | |
| I c-120 | Cl | H | 6-Cl | $i-C_3H_7$ | |
| I c-121 | $CH_3$ | $CH_3$ | H | $i-C_3H_7$ | |
| I c-122 | $CH_3$ | $CH_3$ | 6-$CH_3$ | $i-C_3H_7$ | |
| I c-123 | Cl | $CF_3$ | 6-Cl | $i-C_3H_7$ | |
| I c-124 | Cl | Cl | H | $s-C_4H_9$ | |
| I c-125 | Cl | H | 6-F | $s-C_4H_9$ | |
| I c-126 | Cl | H | 6-Cl | $s-C_4H_9$ | |
| I c-127 | $CH_3$ | $CH_3$ | H | $s-C_4H_9$ | |
| I c-128 | $CH_3$ | $CH_3$ | 6-$CH_3$ | $s-C_4H_9$ | |
| I c-129 | Cl | $CF_3$ | 6-Cl | $s-C_4H_9$ | |
| I c-130 | Cl | Cl | H | phenyl | |
| I c-131 | Cl | H | 6-F | phenyl | |
| I c-132 | Cl | H | 6-Cl | phenyl | |
| I c-133 | $CH_3$ | $CH_3$ | H | phenyl | |
| I c-134 | $CH_3$ | $CH_3$ | 6-$CH_3$ | phenyl | |
| I c-135 | Cl | $CF_3$ | 6-Cl | phenyl | |
| I c-136 | Cl | Cl | H | benzyl | |
| I c-137 | Cl | H | 6-F | benzyl | |
| I c-138 | Cl | H | 6-Cl | benzyl | |
| I c-139 | $CH_3$ | $CH_3$ | H | benzyl | |
| I c-140 | $CH_3$ | $CH_3$ | 6-$CH_3$ | benzyl | |
| I c-141 | Cl | $CF_3$ | 6-Cl | benzyl | |

TABLE 3e

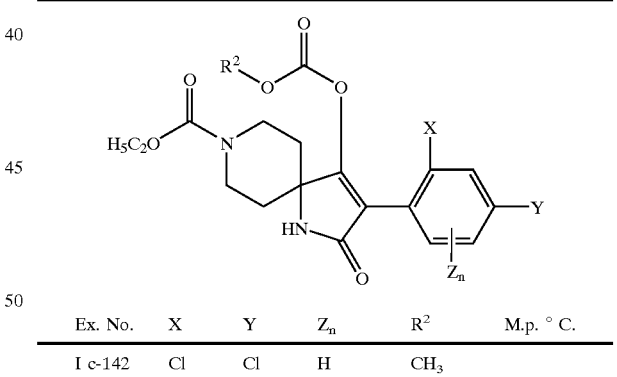

| Ex. No. | X | Y | $Z_n$ | $R^2$ | M.p. °C. |
|---|---|---|---|---|---|
| I c-142 | Cl | Cl | H | $CH_3$ | |
| I c-143 | Cl | H | 6-F | $CH_3$ | |
| I c-144 | Cl | H | 6-Cl | $CH_3$ | |
| I c-145 | $CH_3$ | $CH_3$ | H | $CH_3$ | |
| I c-146 | $CH_3$ | $CH_3$ | 6-$CH_3$ | $CH_3$ | |
| I c-147 | Cl | $CF_3$ | 6-Cl | $CH_3$ | |
| I c-148 | Cl | Cl | H | $C_2H_5$ | |
| I c-149 | Cl | H | 6-F | $C_2H_5$ | |
| I c-150 | Cl | H | 6-Cl | $C_2H_5$ | |
| I c-151 | $CH_3$ | $CH_3$ | H | $C_2H_5$ | |
| I c-152 | $CH_3$ | $CH_3$ | 6-$CH_3$ | $C_2H_5$ | |
| I c-153 | Cl | Cl | H | $i-C_3H_7$ | |
| I c-154 | Cl | H | 6-F | $i-C_3H_7$ | |
| I c-155 | Cl | H | 6-Cl | $i-C_3H_7$ | |
| I c-156 | $CH_3$ | $CH_3$ | H | $i-C_3H_7$ | |
| I c-157 | $CH_3$ | $CH_3$ | 6-$CH_3$ | $i-C_3H_7$ | |
| I c-158 | Cl | $CF_3$ | 6-Cl | $i-C_3H_7$ | |
| I c-159 | Cl | Cl | H | $s-C_4H_9$ | |

TABLE 3e-continued

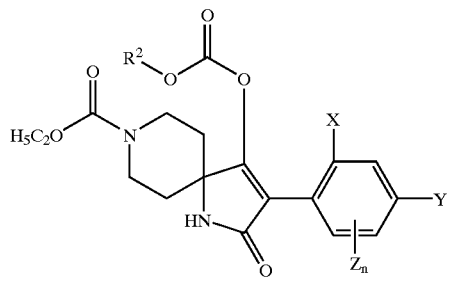

| Ex. No. | X | Y | $Z_n$ | $R^2$ | M.p. °C. |
|---|---|---|---|---|---|
| I c-160 | Cl | H | 6-F | s-$C_4H_9$ | |
| I c-161 | Cl | H | 6-Cl | s-$C_4H_9$ | |
| I c-162 | $CH_3$ | $CH_3$ | H | s-$C_4H_9$ | |
| I c-163 | $CH_3$ | $CH_3$ | 6-$CH_3$ | s-$C_4H_9$ | |
| I c-164 | Cl | $CF_3$ | 6-Cl | s-$C_4H_9$ | |
| I c-165 | Cl | Cl | H | phenyl | |
| I c-166 | Cl | H | 6-F | phenyl | |
| I c-167 | Cl | H | 6-Cl | phenyl | |
| I c-168 | $CH_3$ | $CH_3$ | H | phenyl | |

TABLE 3e-continued

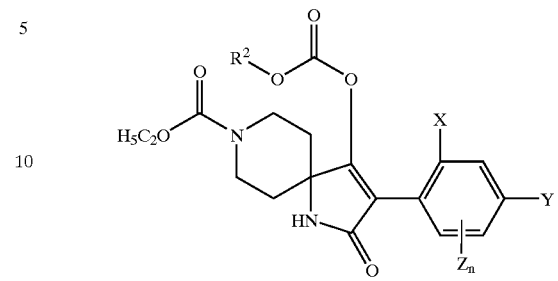

| Ex. No. | X | Y | $Z_n$ | $R^2$ | M.p. °C. |
|---|---|---|---|---|---|
| I c-169 | $CH_3$ | $CH_3$ | 6-$CH_3$ | phenyl | |
| I c-170 | Cl | $CF_3$ | 6-Cl | phenyl | |
| I c-171 | Cl | Cl | H | benzyl | |
| I c-172 | Cl | H | 6-F | benzyl | |
| I c-173 | Cl | H | 6-Cl | benzyl | |
| I c-174 | $CH_3$ | $CH_3$ | H | benzyl | |
| I c-175 | $CH_3$ | $CH_3$ | 6-$CH_3$ | benzyl | |
| I c-176 | Cl | $CF_3$ | 6-Cl | benzyl | |

TABLE 3f

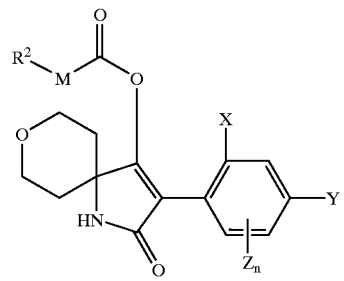

| Ex. No. | X | Y | $Z_n$ | $R^2$ | M | M.p. °C. |
|---|---|---|---|---|---|---|
| I c-177 | Cl | Cl | H | $CH_3$ | O | |
| I c-178 | Cl | H | 6-F | $CH_3$ | O | |
| I c-179 | Cl | H | 6-Cl | $CH_3$ | O | |
| I c-180 | $CH_3$ | $CH_3$ | H | $CH_3$ | O | |
| I c-181 | $CH_3$ | $CH_3$ | 6-$CH_3$ | $CH_3$ | O | 191 |
| I c-182 | Cl | $CF_3$ | 6-Cl | $CH_3$ | O | |
| I c-183 | Cl | Cl | H | $C_2H_5$ | O | 194–196 |
| I c-184 | Cl | H | 6-F | $C_2H_5$ | O | |
| I c-185 | Cl | H | 6-Cl | $C_2H_5$ | O | |
| I c-186 | $CH_3$ | $CH_3$ | H | $C_2H_5$ | O | 188 |
| I c-187 | $CH_3$ | $CH_3$ | 6-$CH_3$ | $C_2H_5$ | O | 193–195 |
| I c-188 | Cl | Cl | H | i-$C_3H_7$ | O | |
| I c-189 | Cl | H | 6-F | i-$C_3H_7$ | O | |
| I c-190 | Cl | H | 6-Cl | i-$C_3H_7$ | O | |
| I c-191 | $CH_3$ | $CH_3$ | H | i-$C_3H_7$ | O | 177 |
| I c-192 | $CH_3$ | $CH_3$ | 6-$CH_3$ | i-$C_3H_7$ | O | 197 |
| I c-193 | Cl | $CF_3$ | 6-Cl | i-$C_3H_7$ | O | |
| I c-194 | Cl | Cl | H | s-$C_4H_9$ | O | 203–205 |
| I c-195 | Cl | H | 6-F | s-$C_4H_9$ | O | |
| I c-196 | Cl | H | 6-Cl | s-$C_4H_9$ | O | |
| I c-197 | $CH_3$ | $CH_3$ | H | s-$C_4H_9$ | O | 151 |
| I c-198 | $CH_3$ | $CH_3$ | 6-$CH_3$ | s-$C_4H_9$ | O | 215–218 |
| I c-199 | Cl | $CF_3$ | 6-Cl | s-$C_4H_9$ | O | |
| I c-200 | Cl | Cl | H | phenyl | O | |

TABLE 3f-continued

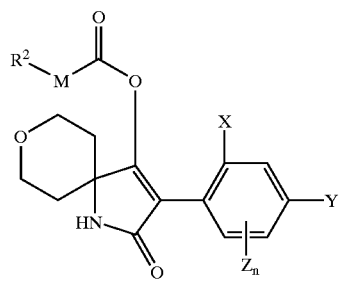

| Ex. No. | X | Y | $Z_n$ | $R^2$ | M | M.p. °C. |
|---|---|---|---|---|---|---|
| I c-201 | Cl | H | 6-F | phenyl | O | |
| I c-202 | Cl | H | 6-Cl | phenyl | O | |
| I c-203 | $CH_3$ | $CH_3$ | H | phenyl | O | |
| I c-204 | $CH_3$ | $CH_3$ | 6-$CH_3$ | phenyl | O | >220 |
| I c-205 | Cl | $CF_3$ | 6-Cl | phenyl | O | |
| I c-206 | Cl | Cl | H | benzyl | O | |
| I c-207 | Cl | H | 6-F | benzyl | O | |
| I c-208 | Cl | H | 6-Cl | benzyl | O | |
| I c-209 | $CH_3$ | $CH_3$ | H | benzyl | O | >220 |
| I c-210 | $CH_3$ | $CH_3$ | 6-$CH_3$ | benzyl | O | 215 |
| I c-211 | Cl | $CF_3$ | 6-Cl | benzyl | O | |
| I c-212 | $CH_3$ | $CH_3$ | H | $H_9C_4$—CH—$CH_2$—<br>           |<br>           $C_2H_5$ | O | 218 |
| I c-213 | $CH_3$ | $CH_3$ | H | i-$C_4H_9$ | O | 178 |
| I c-214 | $CH_3$ | $CH_3$ | 6-$CH_3$ | $(CH_3)_2$CH—$(CH_2)_2$— | S | 185–190 |
| I c-215 | $CH_3$ | $CH_3$ | 6-$CH_3$ | i-$C_3H_7$ | S | 210–215 |
| I c-216 | $CH_3$ | $CH_3$ | 6-$CH_3$ | t-$C_4H_9$ | S | 220–225 |
| I c-217 | $CH_3$ | $CH_3$ | 6-$CH_3$ | i-$C_4H_9$ | O | 188 |
| I c-218 | $CH_3$ | $CH_3$ | 6-$CH_3$ | $H_9C_4$—CH—$CH_2$—<br>           |<br>           $C_2H_5$ | O | 198 |

Example Id-1

5.8 g of the compound of Example Ia-11 in 70 ml of dry methylene chloride are treated with 2.8 ml of triethylamine, and 1.7 g of methanesulphonyl chloride in 5 ml of dry methylene chloride are added at 0 to 10° C. The reaction solution is washed twice using 200 ml of 0.5 N sodium hydroxide solution and dried over magnesium sulphate, and the solvent is distilled off. 3.2 g (56% of theory) remain, m.p. 220° C.

Example I d-1

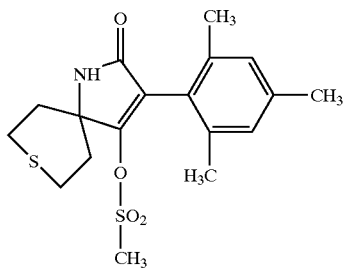

Example Ie-1

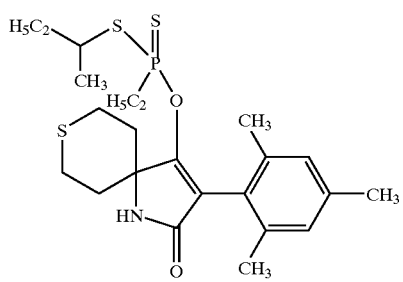

(Ie-1)

3 g of the compound of Example Ia-11 are introduced into 20 ml of dry tetrahydrofuran, the mixture is treated with 1.5 ml of triethylamine, and 2.1 g of sec-butyl ethanethiophosphonothioate are added. The mix is stirred for 1 day at 50° C., the solvent is evaporated, and the residue is chromatographed on silica gel using hexane/acetone 9:1 as the eluant. After the solvent has been evaporated, 1.1 g (=23% of theory) of the above compound of m.p. 216° C. are obtained.

Example (Ie-2) of m.p. 208° C. was obtained analogously:

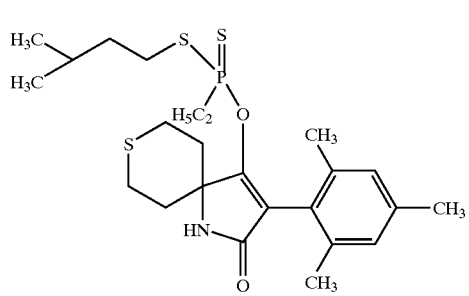
(Ie-2)

Example If-1

5.8 g of the compound of Example Ia-11 in 70 ml of dry methylene chloride are treated with 6.24 ml of tetrabutylammonium hydroxide (in the form of a 40% strength aqueous solution) and the mixture is stirred for 15 minutes at 0 to 10° C. The reaction solution is concentrated and the residue is crystallized by adding diisopropyl ether. After the precipitate has been obtained by filtration with suction, 5.4 g (99% of theory) remain, m.p. 110° C.

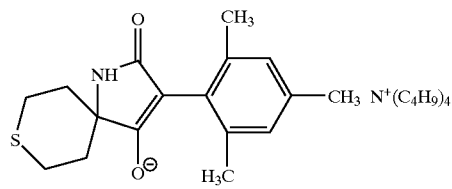
(If-1)

Example Ig-1

5.8 g of the compound of Example Ia-11 in 70 ml of dry methylene chloride are treated with 2.8 ml of triethylamine, and 1.76 ml of morpholinecarbamoyl chloride in 5 ml of dry methylene chloride are added at 0 to 10° C. The reaction solution is washed twice using 200 ml of 0.5 N sodium hydroxide solution and dried over magnesium sulphate, and the solvent is distilled off. 1.2 g (19% of theory) remain, m.p. 198° C.

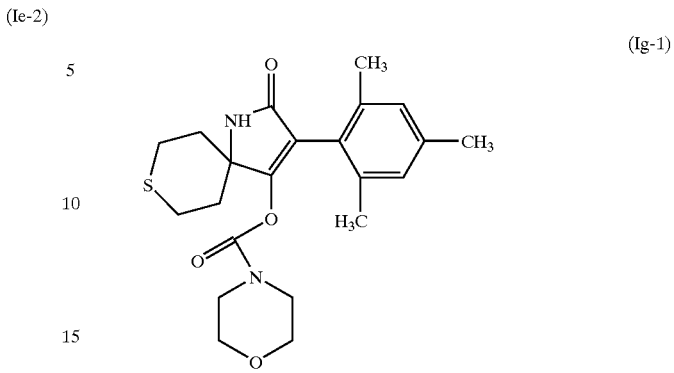
(Ig-1)

Examples for the preparation of intermediates of the formula XVII

Example XVII-1

56 ml of triethylamine are added to 51.2 g of 3-amino-3-cyanothiolane in 600 ml of dry tetrahydrofuran, and a solution of 78.6 g of mesityleneacetyl chloride in 80 ml of dry tetrahydrofuran is added dropwise at 0° C. The reaction mixture is poured into 1.2 l of ice-water, 200 ml of 1 N hydrochloric acid are added, and the precipitate which forms is obtained by filtration with suction and dried. This gives 89.5 g (78% of theory) of the following compound, m.p. 174–175° C.

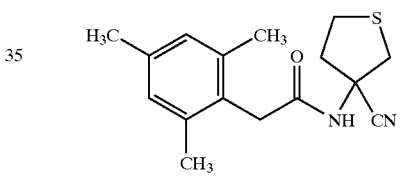

The following compounds XVII are obtained analogously.

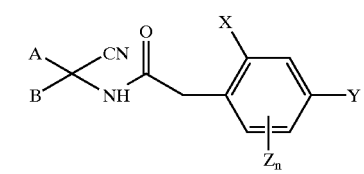
(XVII)

| Ex. No. | X | X | $Z_n$ | A | B | M.p. |
|---|---|---|---|---|---|---|
| XVII-2 | Cl | Cl | H | —(CH$_2$)$_2$—S—CH$_2$— | | 131–133 |
| XVII-3 | CH$_3$ | CH$_3$ | 6-CH$_3$ | —(CH$_2$)$_2$—S—(CH$_2$)$_2$— | | >220 |
| XVII-4 | Cl | Cl | H | —(CH$_2$)$_2$—O—(CH$_2$)$_2$— | | 198–199 |
| XVII-5 | CH$_3$ | CH$_3$ | 6-CH$_3$ | —(CH$_2$)$_2$—O—(CH$_2$)$_2$— | | 182–183 |
| XVII-6 | CH$_3$ | CH$_3$ | 6-CH$_3$ | —(CH$_2$)$_2$—N(CH$_3$)—(CH$_2$)$_2$— | | 176 |
| XVII-7 | CH$_3$ | CH$_3$ | 6-CH$_3$ | —(CH$_2$)$_2$—N(CO—CH$_3$)—(CH$_2$)$_2$— | | 206 |

-continued

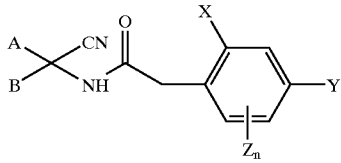

(XVII)

| Ex. No. | X | X | $Z_n$ | A | B | M.p. |
|---|---|---|---|---|---|---|
| XVII-8 | $CH_3$ | $CH_3$ | 6-$CH_3$ | | —$(CH_2)_2$—N—$(CH_2)_2$—<br>　　　　　　\|<br>　　　　　　CO—$C_6H_5$ | 120 |
| XVII-9 | $CH_3$ | CHx3 | 6-$CH_3$ | | —$(CH_2)_2$—N—$(CH_2)_2$—<br>　　　　　　\|<br>　　　　　　CO—$OC_2H_5$ | 161 |
| XVII-10 | $CH_3$ | $CH_3$ | H | —$(CH_2)_2$—O—$(CH_2)_2$— | | 152 |

Examples for the preparation of intermediates of the formula II.

Example II-1

A suspension of 89.5 g of the compound of Example XVII-1 in 500 ml of methylene chloride is added to 152.4 g of concentrated sulphuric acid, stirring is continued for 2 hours, and 218 ml of methanol are added dropwise at 40° C. Stirring is continued for 6 hours at 40–70° C. The reaction solution is poured onto 1.5 l of ice and extracted using 500 ml of methylene chloride, the methylene chloride phase is dried, and the solvent is distilled off. This gives 65 g (65% of theory) of the compound of the formula Example II-1

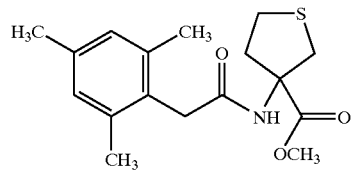

m.p. 111–113° C.

The following compounds of the formula II are obtained analogously:

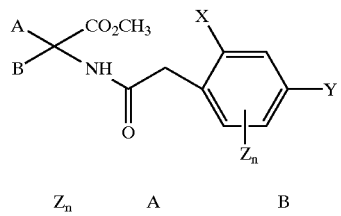

| Ex. No. | X | X | $Z_n$ | A | B | M.p. |
|---|---|---|---|---|---|---|
| II-2 | Cl | Cl | H | —$(CH_2)_2$—S—$CH_2$— | | 133–135 |
| II-3 | $CH_3$ | $CH_3$ | 6-$CH_3$ | —$(CH_2)_2$—S—$(CH_2)_2$— | | 158 |
| II-4 | Cl | Cl | H | —$(CH_2)_2$—O—$(CH_2)_2$— | | 130–131 |
| II-5 | $CH_3$ | $CH_3$ | 6-$CH_3$ | —$(CH_2)_2$—O—$(CH_2)_2$— | | 153–154 |
| II-6 | $CH_3$ | $CH_3$ | 6-$CH_3$ | | —$(CH_2)_2$—N—$(CH_2)_2$—<br>　　　　　　\|<br>　　　　　　$CH_3$ | 128–130 |
| II-7 | $CH_3$ | $CH_3$ | 6-$CH_3$ | | —$(CH_2)_2$—N—$(CH_2)_2$—<br>　　　　　　\|<br>　　　　　　CO—$CH_3$ | 148–150 |
| II-8 | $CH_3$ | $CH_3$ | 6-$CH_3$ | | —$(CH_2)_2$—N—$(CH_2)_2$—<br>　　　　　　\|<br>　　　　　　CO—$C_6H_5$ | oil |
| II-9 | $CH_3$ | $CH_3$ | H | —$(CH_2)_2$—O—$(CH_2)_2$— | | 119 |

The following comparison compounds which are known from the prior art were employed in the use examples:

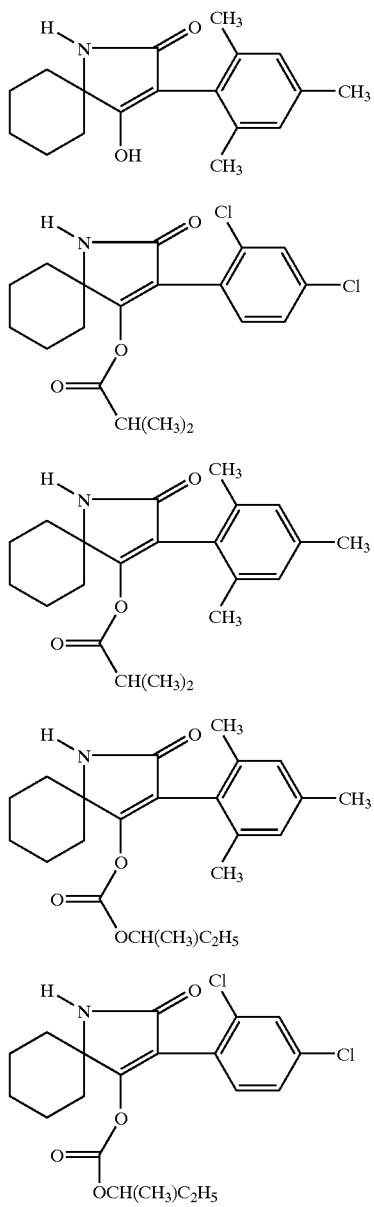

(all disclosed in EP 0456063).

Example A

Myzus Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are severely infested with the green peach apid (*Myzus persicae*) are treated by being dipped into the preparation of active compound of the desired concentration.

After the specified periods of time, the destruction in % is determined. 100% means that all the aphids have been killed; 0% means that none of the aphids have been killed.

In this test, a destruction rate of at least 90% was shown, after 6 days, for example by the compounds of Preparation Examples Ia-17 and Ib-128 at an exemplary active compound concentration of 0.01%, while the prior-art compound (A) resulted in no destruction and the prior-art compound (B) merely achieved a destruction rate of 20% at an active compound concentration of 0.1%.

Example B

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified periods of time, the destruction in % is determined. 100% means that all the caterpillars have been killed; 0% means that none of the caterpillars have been killed.

In this test, a destruction rate of 100% was shown, after 3 days, for example by the compound of Preparation Example Ia-132 at an exemplary active compound concentration of 0.1%.

Example C

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water containing emulsifier to the desired concentration.

Rice seedlings (*Oryza sativa*) are treated by being dipped into the preparation of active compound of the desired concentration and are infested with larvae of the green rice leafhopper (*Nephotettix Cincticeps*) while the leaves are still moist.

After the specified periods of time, the destruction in % is determined. 100% means that all the leafhoppers have been killed; 0% means that none of the leafhoppers have been killed.

In this test, a destruction rate of 100% was shown, for example, by the compounds of Preparation Examples Ic-194 and Ic-198 at an exemplary active compound concentration of 0.01%.

Example D

Tetranychus Test (OP Resistant)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are severely infested with all development stages of the greenhouse red spider mite (*Tetranychus urticae*) are sprayed with an active compound preparation of the desired concentration.

After the specified periods of time, the destruction in % is determined. 100% means that all the spider mites have been killed; 0% means that none of the spider mites have been killed.

In this test, a destruction rate of 100% was shown, after 14 days, for example, by the compounds of Preparation Examples Ia-17, Ib-132 and Ic-198 at an exemplary active compound concentration of 0.02%.

Example E

Panonychus Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water containing emulsifier to the desired concentration.

Young plum trees (*Prunus domestica*) approximately 30 cm in height which are severely infested with all development stages of the fruit tree spider mite (*Panonychus ulmi*) are sprayed with an active compound preparation of the desired concentration.

After the specified periods of time, the destruction in % is determined. 100% means that all the spider mites have been killed; 0% means that none of the spider mites have been killed.

In this test, a destruction rate of 100% was shown, after 14 days, for example, by the compounds of Preparation Examples Ia-17, Ib-132 and Ic-198 at an exemplary active compound concentration of 0.02%.

What is claimed is:

1. A compound of the formula

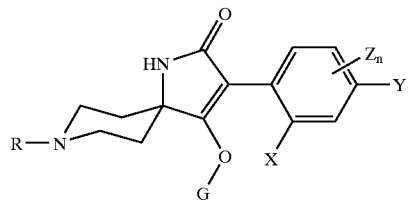

in which

X represents $C_1$–$C_6$-alkyl, halogen or $C_1$–$C_6$-alkoxy,

Y represents hydrogen, $C_1$–$C_6$-alkyl, halogen, $C_1$–$C_6$-alkoxy or $C_1$–$C_3$-halogenalkyl, Z represents $C_1$–$C_6$-alkyl, halogen or $C_1$–$C_6$-alkoxy, R represents $C_1$–$C_6$-alkyl, $C_1$–$C_6$-acyl or $C_1$–$C_6$-alkoxyacyl, G represents hydrogen (a) or the groups (b)

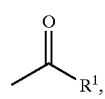

(c)

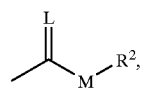

(d)

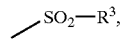

(e)

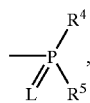

E, (f)

(g)

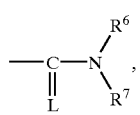

in which

E represents a metal ion equivalent or an ammonium ion,

L represents sulphur or oxygen,

M represents sulphur or oxygen, $R^1$ represents optionally halogen substituted $C_1$–$C_{20}$-alkyl, optionally halogen substituted $C_2$–$C_{10}$-alkenyl, optionally halogen substituted $C_1$–$C_8$-alkoxy-$C_1$–$C_8$-alkyl, optionally halogen substituted $C_1$–$C_8$-alkylthio-$C_1$–$C_8$-alkyl, or represents cycloalkyl which has 3 to 8 ring atoms and which is optionally substituted by $C_1$–$C_8$-alkyl or halogen, or represents phenyl which is optionally substituted by halogen, nitro, $C_1$–$C_8$-alkyl, $C_1$–$C_6$-alkoxy, $C_1$–$C_6$-halogenoalkyl or $C_1$–$C_6$-halogenoalkoxy, or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy, or represents phenoxy-$C_1$–$C_6$-alkyl which is optionally substituted by halogen and/or $C_1$–$C_6$-alkyl, $R^2$ represents optionally halogen substituted $C_1$–$C_{20}$-alkyl, optionally halogen substituted $C_3$–$C_{10}$-alkenyl, optionally halogen substituted $C_1$–$C_8$-alkoxy-$C_2$–$C_8$-alkyl, or represents $C_3$–$C_6$-cycloalkyl which is optionally substituted by $C_1$–$C_6$-alkyl or halogen, or represents phenyl or benzyl, each of which is optionally substituted by halogen, nitro, $C_1$–$C_6$-alkyl, $C_1$–$C_6$-alkoxy or $C_1$–$C_6$-halogenoalkyl, $R^3$, $R^4$ and $R^5$ independently of one another represent $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_3$–$C_5$-alkenylthio, $C_3$–$C_7$-cycloalkylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another represent hydrogen, $C_1$–$C_{10}$-alkyl, $C_3$–$C_{10}$-cycloalkyl, $C_1$–$C_{10}$-alkoxy, $C_3$–$C_8$-alkenyl or $C_1$–$C_8$-alkoxy-$C_1$–$C_8$-alkyl, each of which is optionally substituted by halogen, or represent phenyl which is optionally substituted by halogen, $C_1$–$C_8$-halogenoalkyl, $C_1$–$C_8$-alkyl or $C_1$–$C_8$-alkoxy, or represent benzyl which is optionally substituted by halogen, $C_1$–$C_8$-halogenoalkyl, $C_1$–$C_8$-alkyl or $C_1$–$C_8$-alkoxy, n represents 0 or 3.

2. The compound according to claim 1, in which
X represents $C_1$–$C_4$-alkyl, halogen or $C_1$–$C_4$-alkoxy,
Y represents hydrogen, $C_1$–$C_4$-alkyl, halogen, $C_1$–$C_4$-alkoxy or $C_1$–$C_2$-halogenalkyl,
Z represents $C_1$–$C_4$-alkyl, halogen or $C_1$–$C_4$-alkoxy,
R represents —$CH_3$, —$COCH_3$ or —$CO_2CH_2CH_3$,
G represents hydrogen (a) or the groups

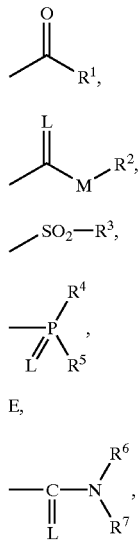

in which
E represents a metal ion equivalent or an ammonium ion,
L represents sulphur or oxygen,
M represents sulphur or oxygen,
$R^1$ represents optionally halogen substituted $C_1$–$C_{16}$-alkyl, optionally halogen substituted $C_2$–$C_8$-alkenyl, optionally halogen substituted $C_1$–$C_6$-alkoxy-$C_1$–$C_6$-alkyl, optionally halogen substituted $C_1$–$C_6$-alkylthio-$C_1$–$C_6$-alkyl,
  or represents cycloalkyl which has 3 to 7 ring atoms and which is optionally substituted by $C_1$–$C_4$-alkyl or halogen,
  or represents phenyl which is optionally substituted by halogen, nitro, $C_1$–$C_4$-alkyl, $C_1$–$C_4$-alkoxy, $C_1$–$C_3$-halogenoalkyl or $C_1$–$C_3$-halogenoalkoxy,
  or represents phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy,
  or represents phenoxy-$C_1$–$C_5$-alkyl which is optionally substituted by fluorine, chlorine, bromine and/or $C_1$–$C_4$-alkyl,
$R^2$ represents optionally halogen substituted $C_1$–$C_{16}$-alkyl, optionally halogen substituted $C_3$–$C_8$-alkenyl, optionally halogen substituted $C_1$–$C_6$-alkoxy-$C_2$–$C_6$-alkyl,
  or represents $C_3$–$C_6$-cycloalkyl which is optionally substituted by fluorine, chlorine or $C_1$–$C_4$-alkyl,
  or represents phenyl or benzyl, each of which is optionally substituted by halogen, nitro, $C_1$–$C_4$-alkyl, $C_1$–$C_3$-alkoxy or $C_1$–$C_3$-halogenoalkyl,
$R^3$, $R^4$ and $R^5$ independently of one another represent $C_1$–$C_6$-alkyl, $C_1$–$C_6$-alkoxy, $C_1$–$C_6$-alkylamino, di-($C_1$–$C_6$)-alkylamino, $C_1$–$C_6$-alkylthio, $C_3$–$C_4$-alkenylthio, $C_3$–$C_6$-cycloalkylthio, each of which is optionally substituted by halogen,
  or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl,
$R^6$ and $R^7$ independently of one another represent hydrogen, $C_1$–$C_8$-alkyl, $C_3$–$C_8$-cycloalkyl, $C_1$–$C_8$-alkoxy, $C_3$–$C_6$-alkenyl or $C_1$–$C_6$-alkoxy-$C_1$–$C_6$-alkyl, each of which is optionally substituted by halogen,
  or represent phenyl which is optionally substituted by halogen, $C_1$–$C_5$-halogenoalkyl, $C_1$–$C_5$-alkyl or $C_1$–$C_5$-alkoxy,
  or represent benzyl which is optionally substituted by halogen, $C_1$–$C_5$-halogenoalkyl, $C_1$–$C_5$-alkyl or $C_1$–$C_5$-alkoxy,
n represents 0 or 2.
3. The compound according to claim 1, in which
X represents methyl, ethyl, propyl, 2-propyl, fluorine, chlorine, bromine, methoxy or ethoxy,
Y represents hydrogen, methyl, ethyl, propyl, i-propyl, butyl, i-butyl, tert-butyl, fluorine, chlorine, bromine, methoxy, ethoxy or trifluoromethyl,
Z represents methyl, ethyl, propyl, i-propyl, butyl, i-butyl, tert-butyl, fluorine, chlorine, bromine, methoxy or ethoxy,
R represents —$CH_3$, —$COCH_3$ or —$CO_2CH_2CH_3$,
G represents hydrogen (a) or the groups

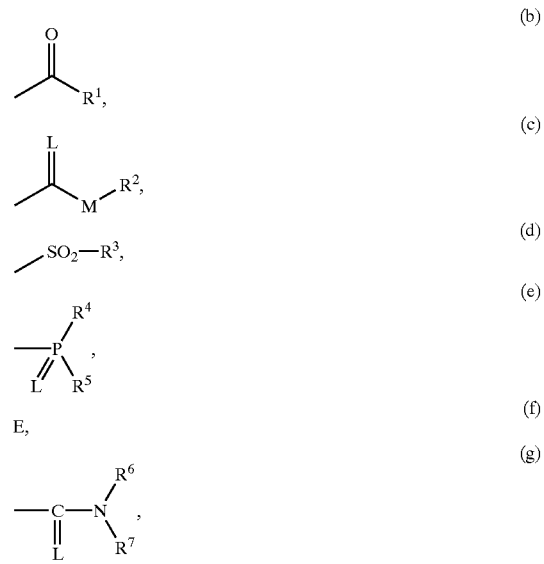

in which
E represents a metal ion equivalent or an ammonium ion,
L represents sulphur or oxygen,
M represents sulphur or oxygen,
$R^1$ represents optionally fluorine or chlorine substituted $C_1$–$C_{14}$-alkyl, optionally fluorine or chlorine substituted $C_2$–$C_6$-alkenyl, optionally fluorine or chlorine substituted $C_1$–$C_4$-alkoxy-$C_1$–$C_6$-alkyl, optionally fluorine or chlorine substituted $C_1$–$C_4$-alkylthio-$C_1$–$C_6$-alkyl,
  or represents cycloalkyl which has 3 to 6 ring atoms and which is optionally substituted by methyl, ethyl, fluorine or chlorine, or represents phenyl which is optionally substituted by fluorine, chlorine, bromine, methyl, ethyl, propyl, i-propyl, methoxy, ethoxy, trifluoromethyl, trifluoromethoxy or nitro, or represents phenyl-$C_1$–$C_3$-alkyl which is optionally substituted by fluorine, chlorine, bromine, methyl, ethyl, propyl, i-propyl, methoxy, ethoxy, trifluoromethyl, trifluoromethoxy or represents phenoxy-$C_1$–$C_4$-alkyl which is optionally substituted by fluorine, chlorine, methyl or ethyl, $R^2$ represents optionally fluorine or chlorine substituted $C_1$–$C_{14}$-alkyl, optionally fluorine or chlorine substituted $C_3$–$C_6$-alkenyl, optionally fluorine or chlorine substituted $C_1$–$C_4$-alkoxy-$C_2$–$C_6$-alkyl, or represents $C_3$–$C_6$-cycloalkyl which is optionally substituted by fluorine, chlorine, methyl or ethyl, or represents phenyl or benzyl, each of which is optionally substituted by fluorine, chlorine, nitro, methyl, ethyl, propyl, i-propyl, methoxy, ethoxy or trifluoromethyl, $R^3$, $R^4$ and $R^5$ independently of one another represent $C_1$–$C_4$-alkyl, $C_1$–$C_4$-alkoxy, $C_1$–$C_4$-alkylamino, di-($C_1$–$C_4$)-alkylamino, $C_1$–$C_4$-alkylthio, each of which is optionally substituted by fluorine or chlorine, or represent phenyl, phenoxy or phenylthio, each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl, $R^6$ and $R^7$ independently of one another represent hydrogen, $C_1$–$C_6$-alkyl, $C_3$–$C_6$-cycloalkyl, $C_1$–$C_6$-alkoxy or $C_1$–$C_6$-alkoxy-$C_1$–$C_4$-alkyl, each of which is optionally substituted by fluorine, chlorine or bromine, or represent phenyl which is optionally substituted by fluorine, chlorine, bromine, $C_1$–$C_4$-halogenoalkyl, $C_1$–$C_4$-alkyl or $C_1$–$C_4$-alkoxy, or represent benzyl which is optionally substituted by fluorine, chlorine, bromine, $C_1$–$C_4$-halogenoalkyl, $C_1$–$C_4$-alkyl or $C_1$–$C_4$-alkoxy, n represents 0 or 1.

4. The compound of claim 1, wherein R represents —$CH_3$, —$COCH_3$ or —$CO_2CH_2CH_3$ and G is hydrogen (a).

5. The compound of claim 1, wherein R represents —$CH_3$, —$COCH_3$ or —$CO_2CH_2CH_3$ and G is the group:

(b)

6. The compound of claim 1, wherein R represents —$CH_3$, —$COCH_3$ or —$CO_2CH_2CH_3$ and G is the group:

(c)

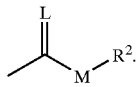

7. The compound of claim 6, wherein G is the group:

(c)

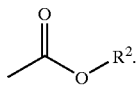

8. An arthropodicidal or nematicidal composition which comprises an effective amount of a compound according to claim 1, and an inert carrier.

9. An arthropodicidal or nematicidal composition which comprises an effective amount of a compound according to any one of claims 4–7, and an inert carrier.

10. A method of combating arthropods or nematodes which comprise applying to said arthropod or nematode or to an environment to which they reside an effective amount of a compound according to claims 1.

11. A method of combating arthropods or nematodes which comprise applying to said arthropod or nematode or to an environment to which they reside an effective amount of a compound according to any one of claims 4–7.

* * * * *

UNITED STATES PATENT AND TRADEMARK OFFICE
CERTIFICATE OF CORRECTION

PATENT NO. : 6,774,133 B2
DATED : August 10, 2004
INVENTOR(S) : Fischer et al.

It is certified that error appears in the above-identified patent and that said Letters Patent is hereby corrected as shown below:

Column 4,
Line 28, "M, Y, Z," should read -- M, X, Y, Z, --.

Column 6,
Line 38, "A, B, Y, Z" should read -- A, B, X, Y, Z --.

Column 7,
Line 35, "formula (VI)" should read -- formula (VII) --.

Column 8,
Line 19, "formula (VI)" should read -- formula (VIII) --.

Column 13,
Line 1, "$C_1 - C_8$-alkyl" should read -- $C_1 - C_4$-alkyl --.

Column 16,
Line 12, "steroisomer. They" should read -- stereoisomer mixtures. They --.

Column 19,
Lines 25-26, "(2,4,trimethylphenyl)" should read -- (2,4,6-trimethylphenyl) --.

Column 21,
Line 1, "formula (XVI)" should read -- formula (XVII) --.

Column 22,
Line 13, "A, B, Y, Z" should read -- A, B, X, Y, Z --.

Column 26,
Line 18, "is character" should read -- is characterized --.

UNITED STATES PATENT AND TRADEMARK OFFICE
CERTIFICATE OF CORRECTION

| | |
|---|---|
| PATENT NO. | : 6,774,133 B2 |
| DATED | : August 10, 2004 |
| INVENTOR(S) | : Fischer et al. |

It is certified that error appears in the above-identified patent and that said Letters Patent is hereby corrected as shown below:

Column 27,
Line 46, "reaction tempt" should read -- reaction temperatures --.

Signed and Sealed this

Twentieth Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,774,133 B2
DATED : August 10, 2004
INVENTOR(S) : Fischer et al.

It is certified that error appears in the above-identified patent and that said Letters Patent is hereby corrected as shown below:

Column 28,
Line 44, "aimides" should read -- amides --.

Column 29,
Lines 13 and 46, "nitrites" should read -- nitriles --.

Column 32,
Line 51, "or pare," should read -- or paraffins --.
Lines 60-61, "montrnorillonite or diatornaceous" should read -- montmorillonite or diatomaceous --.

Column 33,
Line 19, "t nutrients" should read -- trace nutrients --.
Line 57, "(OSOPROTURON)" should read -- (ISOPROTURON) --.
Line 60, "(FENACED)" should read -- (MEFENACET) --.
Lines 60-61, "2-[[((4-methoxymethyl-1,3,5-triazin-2-ylamino)" should read -- 2-[[((4-methoxy-6-methyl-1,3,5-triazin-2-yl)-amino) --.
Line 62, "(METULFURON)" should read -- (METSULFURON) --.
Lines 65-66, "4-ethylamino-2-t-butylainomethylthio-s-triazine" should read
-- 4-ethylamino-2-t-butylamino-6-methylthio-s-triazine --.

Column 34,
Lines 1-2, "(THIAION)" should read -- (THIAMETURON) --.
Line 16, "fenproparin" should read -- fenpropathrin --.

UNITED STATES PATENT AND TRADEMARK OFFICE
CERTIFICATE OF CORRECTION

PATENT NO. : 6,774,133 B2
DATED : August 10, 2004
INVENTOR(S) : Fischer et al.

It is certified that error appears in the above-identified patent and that said Letters Patent is hereby corrected as shown below:

Column 35,
Line 37, "dried This" should read -- dried. This --.

Signed and Sealed this

Twenty-seventh Day of September, 2005

JON W. DUDAS
*Director of the United States Patent and Trademark Office*